(12) United States Patent
Park et al.

(10) Patent No.: US 9,322,044 B2
(45) Date of Patent: Apr. 26, 2016

(54) METHOD FOR PRODUCING PHOSPHOSERINE INCORPORATED PROTEINS BY USING SEPRS MUTANTS AND EF-TU MUTANTS

(71) Applicant: Korea Advanced Institute of Science and Technology, Daejeon (KR)

(72) Inventors: Hee Sung Park, Daejeon (KR); Sangsik Lee, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 39 days.

(21) Appl. No.: 14/210,486

(22) Filed: Mar. 14, 2014

(65) Prior Publication Data
US 2014/0335561 A1 Nov. 13, 2014

(30) Foreign Application Priority Data
May 10, 2013 (KR) .................. 10-2013-0053365

(51) Int. Cl.
C12P 21/00 (2006.01)
C07K 14/47 (2006.01)
C07K 14/245 (2006.01)
C12P 21/02 (2006.01)

(52) U.S. Cl.
CPC .............. C12P 21/00 (2013.01); C07K 14/245 (2013.01); C07K 14/47 (2013.01); C12P 21/02 (2013.01); C12Y 601/01027 (2013.01); Y02P 20/52 (2015.11)

(58) Field of Classification Search
None
See application file for complete search history.

(56) References Cited

U.S. PATENT DOCUMENTS 9,090,928 B2 * 7/2015 Park ................... C12N 15/67
2010/0323364 A1 12/2010 Sekine et al.

FOREIGN PATENT DOCUMENTS

| JP | 2008-61538 A | 3/2008 |
| WO | 2006107813 A2 | 10/2006 |
| WO | 2009099073 A1 | 8/2009 |
| WO | 2012048249 A1 | 4/2012 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Lee, S., et al., "A Facile Strategy for Selective Incorporation of Phosphoserine into Histones", "Angew. Chem. Int. Ed.", Mar. 26, 2013, pp. 5771-5775, vol. 52, No. 22.

* cited by examiner

*Primary Examiner* — Christian Fronda
(74) *Attorney, Agent, or Firm* — Hultquist, PLLC; Steven J. Hultquist

(57) ABSTRACT

The present invention relates to a method of producing a phosphorylated protein using a SepRS (O-phosphoseryl-tRNA synthetase) mutant and an EF-Tu mutant, which have increased activity. More specifically, the invention relates to a method of producing a phosphorylated protein by incorporating phosphoserine into the specific position of a target protein or polypeptide using tRNA$^{Sep}$ serving to recognize at least one codon in the mRNA of the target protein or polypeptide, an O-phosphoseryl-tRNA synthetase (SepRS) mutant selected by a molecular evolution technique and serving to aminoacylate tRNA$^{Sep}$ with phosphoserine (Sep), and an EF-Tu mutant serving to bind and deliver Sep-tRNA$^{Sep}$ to the ribosome.

According to the invention, a phosphorylated protein can be produced in an amount of mg per liter using the SepRS and EF-Tu mutants. Thus, the invention is useful for the production of various phosphorylated proteins, including phosphorylated enzymes, the production of antibodies, the fabrication of protein chips, and cell-based screening for new drug development.

5 Claims, 7 Drawing Sheets

FIG. 2

| Evolution step | | | | | | | | |
|---|---|---|---|---|---|---|---|---|
| | | E$^{412}$ | E$^{414}$ | | | P$^{422}$ | P$^{426}$ | |
| Saturation mutagenesis | | L<br>S<br>D<br>S | A<br>I<br>Y<br>G | | | R<br>S<br>A<br>G | R<br>Y<br>K<br>L | |
| 1$^{st}$ evolution | C$^{348}$ | S<br>V<br>D<br>N<br>S | I<br>S<br>F<br>A<br>G | P$^{445}$ | | S<br>R<br>R<br>A<br>R | R<br>R<br>S<br>K<br>R | ← SepRS6 |
| 2$^{nd}$ evolution | E$^{247}$ D$^{352}$ | S<br>S<br>D | I<br>M<br>W | L$^{452}$ | D$^{461}$ | R<br>R<br>R | R<br>S<br>S | P$^{512}$ ← SepRS9<br>A$^{532}$ |

METHOD FOR PRODUCING PHOSPHOSERINE INCORPORATED PROTEINS BY USING SEPRS MUTANTS AND EF-TU MUTANTS

CROSS-REFERENCE TO RELATED APPLICATION

This application claims priority under the provisions of U.S.C. §119 of Korean Patent Application No. 10-2013-0053365 filed May 10, 2013. The disclosure of such Korean priority patent application is hereby incorporated herein by reference in its entirety, for all purposes.

TECHNICAL FIELD

The present invention relates to a method for producing a phosphorylated protein, and more particularly to a method of producing a phosphorylated protein by incorporating phosphoserine (Sep) into the specific position of a target protein using the SepRS mutant and EF-Tu mutant selected by molecular evolution and to a kit for producing a phosphorylated protein, which comprises the phosphorylated protein.

BACKGROUND ART

Human cells respond to external signals or stimuli in various ways through a signaling process. The signaling process usually includes multi-step biochemical reactions that are generally catalyzed by enzymes and messenger proteins for transferring the signal to the next step. This process often consists of activating a certain enzyme that acts on another enzyme to change the activity of the enzyme. This signaling process either results in a reaction that increases or reduces a certain metabolite or causes significant intracellular changes such as gene expression, cell division or cell death.

The most important reversible covalent modification in cell signaling is protein phosphorylation. A phosphate group ($PO_4$) is reversibly incorporated into a protein by the action of kinase and phosphatase, and the enzymatic activity of the protein is changed due to the incorporated phosphate group. Phosphorylation on serine is the most common, followed by threonine and tyrosine residues. Phosphorylation of protein changes the structure of the protein, and as a result, influences the activity of the protein, the interaction with other proteins, the intracellular distribution of the protein, and the stability of the protein to regulate the function of the protein, thereby influencing cell signaling. Protein phosphorylation usually occurs such that about ⅓ of proteins that are expressed in about 25,000 human genes are phosphorylated. Thus, protein phosphorylation regulates all physiological activities, including cell signaling activity, in eukaryotic organisms including humans. Therefore, when abnormalities in protein phosphorylation are caused by mutations or the like, they cause various diseases such as cancer or neurological diseases. In order to understand cell signaling and elucidate the cause of various diseases attributable to abnormalities in signaling, technology of regulating protein phosphorylation and producing a large amount of a protein phosphorylated at a specific amino acid is essentially required. In addition, this method is necessary for elucidating the function of phosphorylated proteins and developing drugs that regulate the function of phosphorylated proteins related to diseases.

Protein phosphorylation that usually occurs in eukaryotic organisms is very rapid, reversible and multiple, and thus it is very difficult to produce a large amount of a protein, uniformly phosphorylated at a specific amino acid, using eukaryotic cells. In bacteria that are mainly used to produce large amounts of recombinant proteins, a protein phosphorylation mechanism does not exist, and thus it is impossible to produce a phosphorylated protein. Heretofore, various methods (WO 2012/048249, WO 2009/099073, WO 2006/107813, and JP 2008/061538) have been proposed to produce phosphorylated proteins, but among these methods, only the method disclosed in WO 2012/048249 can produce a serine-phosphorylated protein. However, this method has a shortcoming in that, because the efficiency of production of the phosphorylated protein is very low, the phosphorylated protein is produced only in an amount of ug per liter.

Accordingly, the present inventors have made extensive efforts to develop a method of producing a phosphorylated protein with significantly increased efficiency, and as a result, have found that, when a phosphorylated protein is produced using the SepRS and EF-Tu mutants selected by molecular evolution, it is produced in an amount of mg per liter, thereby completing the present invention. This method makes it possible to efficiently produce a protein with site-specific serine phosphorylation, which is one of the most abundant post-translational modifications.

DISCLOSURE OF INVENTION

Technical Problem

It is a main object of the present invention to provide SepRS and EF-Tu mutants selected by molecular evolution.

Another object of the present invention is to provide a recombinant microorganism having introduced therein a gene encoding the SepRS mutant, a gene encoding the EF-Tu mutant, and tRNA$^{Sep}$ gene.

Still another object of the present invention is to provide a kit for producing a phosphorylated protein using the above genes and phosphoserine.

Yet another object of the present invention is to provide a method of producing a phosphorylated protein using the above recombinant microorganism.

Technical Solution

To achieve the above objects, the present invention provides a method of producing a phosphorylated protein, which has phosphoserine (Sep) incorporated into the specific position thereof, using SepRS and EF-Tu mutants selected by molecular evolution.

The present invention also provides an SepRS mutant having at least one mutation selected from among K347E, N352D, E412S, E412D, E414I, E414M, E414W, P495R, P495S, I496R, I496S, and L512I of an O-phosphoseryl-tRNA synthetase (SepRS) having an amino acid sequence of SEQ ID NO:17.

In the present invention, the SepRS mutant may further have at least one mutation selected from among F452L, E481D, and V532A.

The present invention also provides an EF-Tu mutant having at least one mutation selected from among H67R, E216V, E216L, E216T, E216A, E216R, E216C, E216Y, D217G, F219Y, T229S, T229A, W274A, and W274N of an EF-Tu having an amino acid sequence of SEQ ID NO:19.

The present invention also provides a gene encoding the SepRS mutant and a gene encoding the EF-Tu mutant.

The present invention also provides a method of producing a phosphorylated protein by in vitro transcription/expression of a polynucleotide encoding tRNA$^{Sep}$, a polynucleotide encoding the SepRS mutant, a polynucleotide encoding the EF-Tu mutant, and a polynucleotide encoding a target protein or polypeptide.

The present invention also provides a kit for producing a phosphorylated protein, the kit comprising a polynucleotide encoding tRNA$^{Sep}$, a polynucleotide encoding the SepRS mutant, a polynucleotide encoding the EF-Tu mutant, a polynucleotide encoding a target protein or polypeptide, and phosphoserine.

The present invention also provides a recombinant microorganism having introduced therein a gene encoding the SepRS mutant, a gene encoding the EF-Tu mutant, a gene encoding tRNA$^{Sep}$ recognizing at least one codon in the mRNA of a target protein or polypeptide, and a gene encoding the target protein.

The present invention also provides a method for producing a phosphorylated protein, the method comprising the steps of: culturing the above recombinant microorganism to express a phosphorylated target protein having phosphoserine incorporated into the specific position thereof; and recovering the expressed phosphorylated target protein.

Advantageous Effect

The present invention provides a method of producing a phosphorylated protein, which has phosphoserine (Sep) incorporated into the specific position thereof, with high efficiency by the use of the SepRS and EF-Tu mutants selected by molecular evolution.

BRIEF DESCRIPTION OF THE DRAWINGS

FIG. 2 summarizes the amino acid sequences of Mmp SepRS mutants, selected by a molecular evolution technique, in each evolution step. The mutant that shows the highest activity in each evolution step is indicated by the arrow.

BEST MODE FOR CARRYING OUT THE INVENTION

Figure 1:
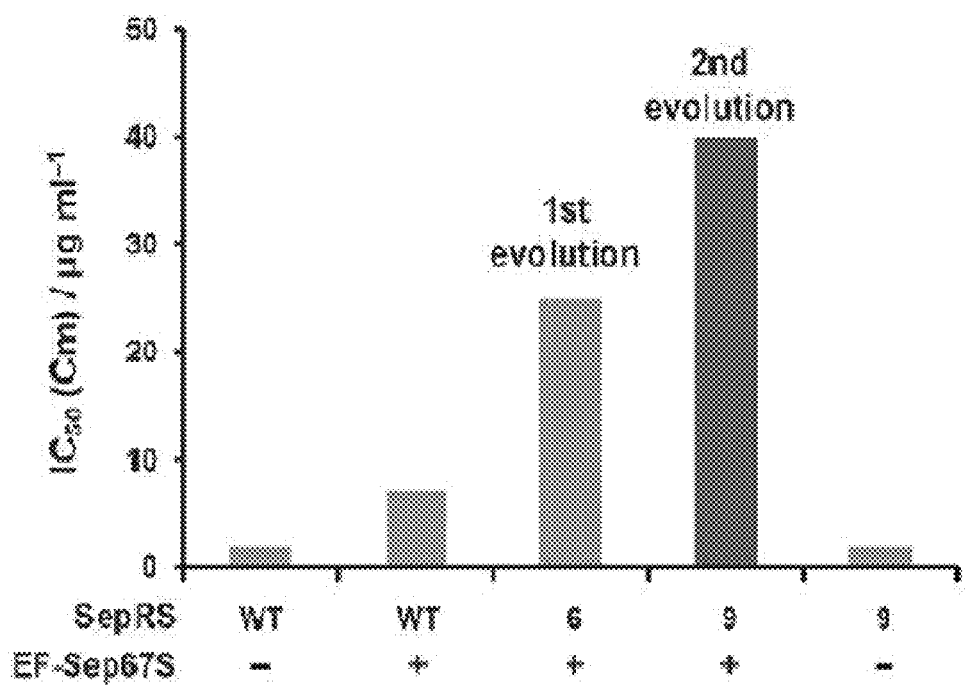
FIG. 1 shows the chloramphenicol resistance (IC 50, ug/ml) of an *E. coli* strain that includes an amber stop codon (UAG) inserted into the 112$^{th}$ amino acid (asp) position of chloramphenicol acetyltransferase (CAT) and that has tRNA$^{Sep}$ and a combination of SepRS mutants (SepRS6 or SepRS9) expressed together with EF-Sep67S. The *E. coli* strain was *E. coli* Top10ΔserB, and the selection process was performed on an LB plate medium having 2 mM phosphoserine (Sep) and various concentrations of chloramphenicol.

Unless defined otherwise, all technical and scientific terms used herein have the same meaning as commonly understood by one of ordinary skill in the art to which the invention pertains. Generally, the nomenclature used herein and the experiment methods are those well known and commonly employed in the art.

As used herein, the term "tRNA$^{Sep}$" refers to a tRNA that binds to O-phosphoserine (Sep) and recognizes at least one codon so as to incorporate phosphoserine (Sep) into a protein or polypeptide. In some embodiments, the tRNA$^{Sep}$ includes an anticodon that is derived from *Methanocaldococcus jannaschii* containing a C20U mutation having increased binding affinity for SepRS and that binds to a stop codon.

As used herein, the term "O-phosphoseryl-tRNA synthetase (SepRS)" refers to a class II-type O-phosphoseryl-tRNA synthetase that aminoacylates tRNA$^{Sep}$ with O-phosphoserine (Sep).

As used herein, the term "EF-Tu" refers to an elongation factor that binds and delivers an aminoacylated tRNA to the ribosome.

A conventional method for producing a phosphorylated target protein is disclosed in WO 2012/048249. In this method, the codon of an mRNA encoding the specific amino acid of the target protein is replaced by an amber stop codon (UAG), and phosphoserine is incorporated into the specific position of the target protein using tRNA$^{Sep}$, SepRS, EF-Sep (EF-Tu mutant) and the mRNA, thereby producing a phosphorylated protein. This method has a shortcoming in that the phosphorylated target protein is produced only in an amount of ug per liter.

In the present invention, in order to increase the efficiency of production of a phosphorylated target protein and increase the amount of production of the protein to an amount of mg per liter, SepRS and EF-Tu mutants were selected by molecular evolution. It was shown that the use of the selected mutants greatly increased the amount of production of the phosphorylated target protein from a level of 25 ug (MEK1) per liter to a level of 3 mg per liter.

In other words, in an example of the present invention, molecular evolution was used to obtain the SepRS and EF-Tu mutants having high activities. Specifically, the method of the present invention may comprise randomly mutating a target protein-encoding gene by a DNA shuffling technique to obtain a library of gene mutants (diversification step), selecting a mutant having desired activity from the gene mutant library (selection step), and sequencing the DNA in order to determine the portion of the mutant in which a mutation occurred (amplification step). Thus, in the present invention, mutants having increased activity could be isolated using *E.* coli strains transformed with an enzyme mutant library obtained by a DNA shuffling technique using normal SepRS or EF-Tu as a template.

Thus, in one aspect, the present invention is directed to an SepRS mutant having at least one mutation selected from among K347E (K (lysine)-to-E (glutamic acid) substitution at amino acid position 347), N352D (N (asparagine)-to-D (aspartic acid) substitution at amino acid position 352), E412S (E (glutamic acid)-to-S(serine) substitution at amino acid position 412), E412D (E (glutamic acid)-to-D (aspartic acid) substitution at amino acid position 412), E414I (E (glutamic acid)-to-I (isoleucine) substitution at amino acid position 414), E414M (E (glutamic acid)-to-M (methionine) substitution at amino acid position 414), E414W (E (glutamic acid)-to-W (tryptophan) substitution at amino acid position 414), P495R (P (proline))-to-R (arginine) substitution at amino acid position 495), P495S (P (proline)-to-S(serine) substitution at amino acid position 495), I496R (I (isoleucine)-to-R (arginine) substitution at amino acid position 496), I496S (I (isoleucine)-to-S(serine) substitution at amino acid position 496), and L512I (L (leucine)-to-I (isoleucine) substitution at amino acid position 512) of an O-phosphoseryl-tRNA synthetase (SepRS) having an amino acid sequence of SEQ ID NO: 17.

In another aspect, the present invention is also directed to an EF-Tu mutant having at least one mutation selected from among H67R (H (histidine)-to-R (arginine) substitution at amino acid position 67), E216V (E (glutamic acid)-to-N(asparagine) substitution at amino acid position 216), E216L (E (glutamic acid)-to-L (leucine) substitution at amino acid position 216), E216T (E (glutamic acid)-to-T (threonine) substitution at amino acid position 216), E216A (E (glutamic acid)-to-A (alanine) substitution at amino acid position 216), E216R (E (glutamic acid)-to-R (arginine) substitution at amino acid position 216), E216C (E (glutamic acid)-to-C (cysteine) substitution at amino acid position 216), E216Y (E (glutamic acid)-to-Y (tyrosine) substitution at amino acid position 216), D217G (D (aspartic acid-to-G (glycine) substitution at amino acid position 217), F219Y (F (phenylalanine)-to-Y (tyrosine) substitution at amino acid position 219), T229A (T (threonine)-to-A (alanine) substitution at amino acid position 229), T229S (T (threonine)-to-S(serine) substitution at amino acid position 229), W274A (W (tryptophan)-to-A (alanine) substitution at amino acid position 274), and W274N (W (tryptophan)-to-N (asparagine) substitution at amino acid position 274) of an EF-Tu having an amino acid sequence of SEQ ID NO: 19.

In the present invention, the SepRS mutant may further have at least one mutation selected from among F452L (F (phenylalanine)-to-L (leucine) substitution at amino acid position 452), E481D (E (glutamic acid)-to-D (aspartic acid) substitution at amino acid position 481), and V532A (V (valine)-to-A (alanine) substitution at amino acid position 532.

SEQ ID NO: 17 is the amino acid sequence of a SepRS isolated from *Methanococcus maripaludis*, and a gene encoding the SepRS has a nucleotide sequence of SEQ ID NO: 18.

For example, mutants containing some of the above-described substitutions also fall within the scope of the present invention, and the SepRS mutant may have an amino acid sequence of any one of SEQ ID NOs: 1 to 4.

SEQ ID NO: 19 is the amino acid sequence of an EF-Tu (elongation factor) isolated from *E. coli*, and a gene encoding the EF-Tu has a nucleotide sequence of SEQ ID NO: 20.

For example, mutants containing some of the above-described substitutions also fall within the scope of the present invention, and the EF-Tu mutant may have an amino acid sequence of any one of SEQ ID NOs: 6 to 14.

Examples of the SepRS mutant and the EF-Tu mutant are shown in Table 1 below.

TABLE 1

| SEQ ID NOs: | Mutations |
|---|---|
| 1 | K347E, N352D, E412S, E414I, P495R, I496R, L512I |
| 2 | E412S, E414M, F452L, P495R, I496S |
| 3 | E412D, E414W, E481D, P495R, I496S, V532A |
| 4 | E412S, E414I, P495S, I496R |
| 6 | H67R, E216V, D217G, F219Y, T229S, W274N |
| 7 | H67R, E216A, D217G, F219Y, T229S, W274N |
| 8 | H67R, E216N, D217G, F219Y, T229A, W274N |
| 9 | H67R, E216N, D217G, F219Y, T229S, W274A |
| 10 | H67R, E216Y, D217G, F219Y, T229S, W274N |
| 11 | H67R, E216C, D217G, F219Y, T229S, W274N |
| 12 | H67R, E216R, D217G, F219Y, T229S, W274N |
| 13 | H67R, E216T, D217G, F219Y, T229S, W274N |
| 14 | H67R, E216L, D217G, F219Y, T229S, W274N |

In still another aspect, the present invention is also directed to a gene encoding the SepRS mutant and a gene encoding the EF-Tu mutant.

In the present invention, a gene encoding the SepRS mutant may be a gene encoding an amino acid sequence of any one of SEQ ID NOs: 1 to 4, and a gene encoding the EF-Tu mutant may be a gene encoding an amino acid sequence of any one of SEQ ID NOs: 6 to 14.

In the present invention, tRNA$^{Sep}$ functions to bind to O-phosphoserine (Sep) and recognize at least one codon so as to incorporate phosphoserine (Sep) into a protein or polypeptide.

For example, tRNA$^{Sep}$ derived from *Methanocaldococcus jannaschii* has a nucleotide sequence of SEQ ID NO: 16.

In addition, the present invention may encompass an amino acid sequence or nucleotide sequence that has a mutation selected from among substitution, deletion, insertion and addition of one or more residues in the amino acid or nucleotide sequence of any one of the above-described sequences and has a sequence identity of at least 70%, 80%, 90% or 95% to that of the amino acid sequence or nucleotide sequence of the present invention.

As used herein, the term "sequence identity" refers to residue sequence similarity between two polynucleotide or polypeptide sequences. "Sequence identity" may be determined by comparing the two sequences aligned in the optimum state over the region of the amino acid or nucleotide sequence to be compared. Herein, the polynucleotide or polypeptide to be compared may have an addition or a deletion (e.g., gap, overhang or the like) compared to a reference sequence (for example, consensus sequence or the like) for the optimum alignment of the two sequences. Numerical values of sequence identity can be calculated by identifying the same nucleic acid bases or amino acids present in both sequences to determine the number of fitting sites, then dividing the number of fitting sites by the total number of bases or amino acids in the sequence region to be compared, and multiplying the obtained numerical value by 100. The sequence identity between nucleic acid and amino acid sequences may be measured, for example, by sequence analysis software, particularly BLASTN, BLASTP, FASTA or the like. BLASTN and BLASTP are generally available from http://www.ncbi.nlm.nih.gov/BLAST/.

It will be obvious to those skilled in the art that a phosphorylated target protein can be produced by transcribing/translating polynucleotides, which encode tRNA$^{Sep}$, the SepRS mutant and the EF-Tu mutant, in vitro before or together with a polynucleotide encoding the target protein.

In yet another aspect, the present invention is directed to a method of producing a phosphorylated protein either by in vitro transcription/expression of a polynucleotide encoding tRNA$^{Sep}$, a polynucleotide encoding an SepRS mutant, and a polynucleotide encoding an EF-Tu mutant, or by in vitro transcription/expression of the polynucleotide encoding tRNA$^{Sep}$, the polynucleotide encoding the SepRS mutant, and the polynucleotide encoding the EF-Tu mutant together with a polynucleotide encoding a target protein or polypeptide.

The inventive method of producing a phosphorylated protein by in vitro transcription/translation may include the following system: the rabbit reticulocyte system, the E. coli S-30 transcription-translation system, or the wheat germ based translational system. Combined transcription/translation systems are available, in which both phage RNA polymerases (such as T7 or SP6) and eukaryotic ribosomes are present. One example of a kit is the TNT® system from Promega Corporation. This system generally includes amino acids, ribosomes, tRNAs, synthetases, and mRNA. Specifically, the system includes extracts containing all the macromolecular components (70S or 80S ribosomes, tRNAs, aminoacyl-tRNA synthetases, initiation, elongation and termination factors, etc.) required for in vitro expression. To ensure efficient translation, each extract is supplemented with amino acids, energy sources (ATP, GTP), energy regenerating systems (creatine phosphate and creatine phosphokinase for eukaryotic systems, and phosphoenol pyruvate and pyruvate kinase), and other co-factors ($Mg^{2+}$, $K^+$, etc.).

The mRNA is not required to have a poly(A) tail, if having a poly(A) tail is essential for some other purpose, a vector may be used that has a stretch of about 100 adenine (A) residues incorporated into the polylinker region. In addition, eukaryotic ribosomes read RNAs that have a 5' methyl guanosine cap more efficiently. RNA caps can be incorporated by initiation of transcription using a capped base analogue, or adding a cap in a separate in vitro reaction post-transcriptionally In another example of the present invention, a recombinant microorganism was prepared, which has introduced therein a gene encoding the SepRS mutant, a gene encoding the EF-Tu mutant, tRNA$^{Sep}$ recognizing at least one codon in the mRNA of a target protein or polypeptide, and a gene encoding the target protein, and then the recombinant microorganism was cultured. As a result, it could be seen that a phosphorylated target protein was produced in an amount of mg per liter.

Therefore, in a further aspect, the present invention is directed to a recombinant microorganism having introduced therein a gene encoding the SepRS mutant, a gene encoding the EF-Tu mutant, a gene encoding tRNA$^{Sep}$ recognizing at least one codon in the mRNA of a target protein or polypeptide, and a gene encoding the target protein, and a method for producing a phosphorylated protein, the method comprising the steps of: culturing the above recombinant microorganism to express a phosphorylated target protein having phosphoserine incorporated into the specific position thereof; and recovering the expressed phosphorylated target protein.

In the present invention, the gene encoding the SepRS mutant may be a gene that further encodes at least one mutation selected from among F452L, E481D and V532A. Particularly, the gene encoding the SepRS mutant may have a nucleotide sequence set forth in SEQ ID NO: 5.

In the present invention, the gene encoding the EF-Tu mutant may have a nucleotide sequence set forth in SEQ ID NO: 15.

In the present invention, the gene encoding the tRNA$^{Sep}$ may have a nucleotide sequence set forth in SEQ ID NO: 16.

In the present invention, the microorganism may be selected from the group consisting of bacteria, archaea and eukaryotic cells. Particularly, the microorganism may be E. coli.

In the present invention, "the gene expression controlling system" is a system that controls the expression of nucleic acids when the nucleic acids are introduced into transcription/expression systems or microorganisms. For example, genes that are introduced into viral and retroviral systems usually contain promoters and/or enhancers to help control the expression thereof. A promoter is generally a sequence or sequences that function when in a relatively fixed location in regard to the transcription start site. A promoter contains core elements required for basic interaction of RNA polymerase and transcription factors, and may contain upstream elements and response elements.

Suitable promoters are generally obtained from viral genomes (e.g., polyoma, Simian Virus 40 (SV40), adenovirus, retroviruses, hepatitis-B virus, and cytomegalovirus) or heterologous mammalian genes (e.g. beta actin promoter). Enhancer generally refers to a sequence of DNA that functions at no fixed distance from the transcription start site and can be either 5' or 3' to the transcription unit. Furthermore, enhancers can be within an intron as well as within the coding sequence itself. Most enhancers are between 10 and 300 bp in length, and they function in cis. Enhancers function to increase transcription from nearby promoters. Enhancers also often contain response elements that mediate the regulation of transcription. Many enhancer sequences are now known from mammalian genes (globin, elastase, albumin, α-fetoprotein and insulin). However, enhancers from a eukaryotic cell virus are usually used for general gene expression. Suitable examples include the SV40 enhancer on the late side of the replication origin, the cytomegalovirus early promoter enhancer, the polyoma enhancer on the late side of the replication origin, and adenovirus enhancers.

In certain embodiments, the promoter and the enhancer can act as a constitutive promoter and enhancer to maximize the transcription of the target gene. In certain constructs, the promoter and the enhancer region are active in all eukaryotic cell types, even if they are only expressed in a particular type of cell at a particular time. A preferred promoter of this type is the CMV promoter. In other embodiments, the promoter and the enhancer are tissue or cell specific.

In certain embodiments, the promoter and the enhancer are inducible. Induction can occur, e.g., as the result of a physiologic response, a response to outside signals, or as the result of artificial manipulation. Such promoters are well known to those of skill in the art. For example, in some embodiments, the promoter and the enhancer may be specifically activated either by light or specific chemical events which trigger their function. There are also ways to enhance viral vector gene expression by exposure to irradiation, such as gamma irradiation, or alkylating chemotherapy drugs.

Expression vectors used in eukaryotic host cells (yeast, fungi, insect, plant, animal, human or nucleated cells) may also contain sequences necessary for the termination of transcription which may affect mRNA expression. These sequences are transcribed as polyadenylated segments in the 3' untranslated portion of the mRNA encoding the target protein. The 3' untranslated regions also include transcription termination sites. Usually, the transcription unit contains a polyadenylation region. One benefit of this region is that it increases the likelihood that the transcribed unit will be processed and transported like mRNA. The identification and use of polyadenylation signals in expression constructs is well known to those skilled in the art. It is preferred that homologous polyadenylation signals be used in the transgene constructs.

The gene encoding the tRNA$^{Sep}$, the gene encoding the SepRS mutant, and the gene encoding a mutant elongation factor of each host corresponding to the EF-Tu mutant should be introduced into suitable organisms in a state in which they are operably linked to one or more expression control sequences. Herein, suitable organisms include bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems.

It will be obvious to one of ordinary skill in the art that regardless of the system used (i.e., in vitro or in vivo), expression of the gene encoding the tRNA$^{Sep}$, the gene encoding the SepRS mutant, and the gene encoding a mutant elongation factor of each host cell having a mutation corresponding to the EF-Tu mutant will result in site-specific incorporation of phosphoserine into the target protein that is translated in the system.

Suitable prokaryotic host cells may be *E. coli* cells, and examples thereof include *E. coli* JM109, *E. coli* DH5α, *E. coli* JM101, *E. coli* K12, *E. coli* W3110, *E. coli* X1776, *E. coli* XL1-Blue (Stratagene, USA), *E. coli* B, *E. coli* B21(DE3), *E. coli* TOP10 and the like. *E. coli* strains such as FMB101, NM522, NM538 and NM539, and other prokaryotic species and genera may also be used. In addition to the above-described *E. coli* strains, *Agrobacterium* sp. strains such as *Agrobacterium* A4, bacilli such as *Bacillus subtilis*, other enterobacteria such as *Salmonella typhimurium* or *Serratia marcescens*, and various *Pseudomonas* sp. strains may be used as host cells. Known eukaryotic host cells such as yeast and mold, insect cells such as *spodoptera frugiperda* (SF9), animal cells such as Chinese hamster ovary (CHO) cells and mouse cells, and tissue-cultured human and plant cells may be used as host cells. The protein produced in prokaryotic host cells may include methionine at the N-terminus to help the expression of the target protein. The N-terminal methionine can be cleaved. Promoters that are mainly used in vectors for expression in recombinant prokaryotic host cells are the lactamase and lactose promoter systems. The recombinant vectors further have a marker gene for selection.

In addition, yeasts suitable as host cells may be *Saccharomyces*, *Pichia*, *K. Actinomycetes* and *Kluyveromyces*, and other species and genera may also be used. Yeast vectors may contain an origin of replication, an autonomously replicating sequence (ARS), a promoter, a sequence for polyadenylation, a sequence for transcription termination, and a marker gene for selection. Particularly suitable promoters for yeast include metallothionein, 3-phosphoglycerate kinase (Hitzeman et al., *J. Biol. Chem.* 255:2073, (1980)) or glycolytic enzymes (Holland et al., *Biochem.* 17:4900, (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase. Other suitable vectors and promoters for use in yeast expression are described in Fleer et al., *Gene*, 107:285-195 (1991), in Li, et al., *Lett Appl Microbiol.* 40(5):347-52 (2005), Jansen, et al., *Gene* 344:43-51 (2005) and Daly and Hearn, *J. Mol. Recognit.* 18(2):119-38 (2005). The above promoters and vectors are well known to those skilled in the art.

Insect or mammalian host cells well known to those skilled in the art may also be used to incorporate tRNA$^{Sep}$, a recombinant EF-Tu mutant and a recombinant SepRS mutant into the specific position of a target protein or polypeptide by expression. Commonly used promoter sequences and enhancer sequences are derived from Polyoma virus, Adenovirus 2, Simian Virus 40 (SV40), and human cytomegalovirus. Exemplary expression vectors for use in mammalian host cells are well known to those skilled in the art.

There are a number of methods which can be used to deliver desired nucleic acids to cells. These methods can largely be divided into two classes: viral based delivery methods and non-viral based delivery methods. For example, nucleic acids can be delivered through a number of direct delivery systems such as electroporation, lipofection, calcium phosphate precipitation, plasmids, viral vectors, viral nucleic acids, phage nucleic acids, phages, cosmids, or via transfer of genetic material in carriers such as cationic liposomes. These methods are well known to those skilled in the art and can be easily applied using the compositions and methods described herein.

Transfer vectors can be any nucleotide construction used to deliver genetic material into cells. In some embodiments, the vectors are derived from either a virus or a retrovirus. Viral vectors include Adenovirus, Adeno-associated virus, Herpes virus, Vaccinia virus, Polio virus, AIDS virus, neuronal trophic virus, Sindbis and other RNA viruses, including HIV-based viruses.

Typically, viral vectors contain nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a desired gene or gene/promoter cassette is inserted into the viral genome in place of the removed viral DNA. The functions of the removed early genes are typically supplied by cell lines which have been engineered to express the gene products of the early genes in trans.

Nucleic acids can also be delivered through electroporation, sonoporation, lipofection, or calcium phosphate precipitation. Lipofection involves the use liposomes, including cationic liposomes (e.g., DOTMA, DOPE, DC-cholesterol) and anionic liposomes, to delivery genetic material to a cell. Commercially available liposome kits include LIPOFECTIN, LIPOFECTAMINE (GIBCO-BRL, Inc., Gaithersburg, Md.), SUPERFECT (Qiagen, Inc. Hilden, Germany), and TRANSFECTAM (PromegaBiotec, Inc., Madison, Wis.).

Nucleic acids that are to be integrated into the host cell genome typically contain integration sequences. These sequences are often viral related sequences, particularly when viral based systems are used for delivery. These viral intergration systems can also be used in a non-nucleic acid based system of deliver, such as a liposome. Known techniques for integration of genetic material into a host genome include methods designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

In the method for producing the target protein according to the present invention, the phosphorylated protein can be purified, either partially or substantially to homogeneity, according to standard procedures known to and used by those of skill in the art including, but not limited to, ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, and gel electrophoresis. A protein refolding step can be performed to make a correctly folded mature protein. High-performance liquid chromatography (HPLC), affinity chromatography or other suitable methods can be employed to obtain the protein in higher purity. In one embodiment, the phosphorylated target protein is purified by an affinity-based purification technique using an antibody against a protein containing phosphoserine. The phosphorylated protein purified, partially or to homogeneity, may be used as an antigen for antibody production, a therapeutic reagent, an assay reagent, etc.

Those of skill in the art will recognize that, after synthesis, expression and purification, proteins can possess conformations different from the desired conformations. For example, proteins or polypeptides produced by prokaryotic systems are often optimized by exposure to chaotropic agents to achieve proper folding. During purification from lysates derived from *E. coli*, the expressed protein is optionally denatured and then renatured. This is accomplished by solubilizing the proteins in a chaotropic agent such as guanidine HCl.

In a still further aspect, the present invention is directed to a kit for producing a phosphorylated protein, the kit comprising a polynucleotide encoding tRNA$^{Sep}$, a polynucleotide encoding a SepRS mutant, and a polynucleotide encoding an EF-Tu mutant.

A kit according to the present invention comprises the components of a conventional kit and may further comprise host cells that express phosphoserine (Sep), a polynucleotide encoding tRNA$^{Sep}$, a polynucleotide encoding the SepRS mutant and a polynucleotide encoding the EF-Tu mutant.

The kit may include an external package that may include instructions regarding the use of the components.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Construction of Gene Library of SepRS and EF-Tu Mutants (1) Construction of SepRS Mutants Identification of SepRS having activity of incorporating phosphoserine (Sep) with higher efficiency in *E. coli* was performed using molecular evolution technology. According to the structure of a SepRS:tRNA$^{Cys}$ complex from *Archaeoglobus fulgidus* (R. Fukunaga, et al., *Nat Struct Mol Biol* 2007, 14, 272), four amino acids (glutamic acid (Glu) at position 412, glutamic acid (Glu) at position 414, proline (Pro) at position 495 and isoleucine (Ile) at position 496) were selected from the anticodon binding site of *Methanococcus maripaludis* SepRS (Mmp SepRS) and subjected to molecular evolution. Before performing the molecular evolution, for each library construction, PCR for changing the surrounding nucleotides to increase the GC content compared to the AT content in the wobble position of the codon was performed. PCR was performed using Mmp SepRS of SEQ ID NO: 17 as a template and the primers used are as follows:

```
SEQ ID NO: 21:
SP412GCF1, 5'-GAA GAG GGC AAG AAC CTG CTC

GGA CCT TCA ATT TTA AAC G-3';

SEQ ID NO: 22:
SP412GCF2, 5'-CGT GAA GAT CAA CAT CTT CGA

AAA AGA AGA GGG CAA GAA CCT G-3';

SEQ ID NO: 23:
SP412GCR, 5'-GAA GAT GTT GAT CTT CAC GTT

TTT CTT GGT TTT TCC AAA TG-3';

SEQ ID NO: 24:
SP130F, 5'-CGA TGG AAA TGT AAT TGG CAT

TCC TGA AGC TTG ACG-3';

SEQ ID NO: 25:
SP130R, 5'-CCA ATT ACA TTT CCA TCG-3';

SEQ ID NO: 26:
SP495GCF, 5'-GAG TTC AAG GTC AAG GTG CCA

ATT GTC AGA AGT TTA AGC G-3';

SEQ ID NO: 27:
SP495GCR, 5'-CAC CTT GAC CTT GAA CTC AGT

AGT GTT TGA CAC AAA TGC-3.
```

The template vector pKD-SepRS-EFSep67S for library construction was made using a forward primer (SEQ ID NO 28: EF67SF, 5'-GTA TCA CCA TCA ACA CTT CTT CCG TTG AAT ACG ACA CCC CG-3') and a reverse primer (SEQ ID NO 29: EF67R, 5'-AGA AGT GTT GAT GGT GAT AC-3). Based on the template vector, PCR for randomly mutating the four amino acids was performed using the following primer combination (Park H-S et al., *Science* 2006, 311:535-538):

```
SEQ ID NO: 30:
SP412X414XF, 5'-GTG AAG ATC AAC ATC TTC

NNS AAA NNS GAG GGC AAG AAC CTG CTC-3';

SEQ ID NO: 31:
SP412414R, 5'-GAA GAT GTT GAT CTT CAC G-3';

SEQ ID NO: 32:
SP495X496XF, 5'-GAG TTC AAG GTC AAG GTG

NNS NNS GTC AGA AGT TTA AGC GAC-3';

SEQ ID NO: 33:
SP495496R, 5'-CAC CTT GAC CTT GAA CTC-3';

SEQ ID NO: 34:
SP263F, 5'-CAA TTT GGC TTT ACA AAC TTT

GAA TTC ATT CCT GAT GAA AAG-3';

SEQ ID NO: 35:
EF67R, 5'-AGA AGT GTT GAT GGT GAT AC-3'.
```

The resulting PCR products were purified by agarose gel extraction, after which the PCR products were treated with the restriction enzymes EcoRI and SalI and ligated with a pKD-SepRS-EFSep67S vector treated with the same restriction enzymes. Then, the vectors were transformed into an *E. coli* Top10ΔserB strain having pCAT112TAG-SepT (H. S. Park, et al., *Science* 2011, 333, 1151.), thereby constructing a library of 1.6×10⁶ SepRS mutants.

The library was subjected to a selection process using the activity of chloramphenicol acetyltransferase (CAT). Specifically, the library was cultured on an LB plate medium containing 30 μg/ml of chloramphenicol (Cm), 25 μg/ml of kanamycin (Kan), 10 μg/ml of tetracycline (Tc) and 0.05 mM IPTG (isopropyl-β-D-thiogalactopyranoside) at 30° C. for 60 hours (H. S. Park, et al., *Science* 2011, 333, 1151.). As a result, about 4,000 positive colonies were selected. pKD-SepRS-EFSep67S and pCAT112TAG-SepT were isolated from the colonies by agarose gel extraction, and then the chloramphenicol resistance of each of the clones was measured in the chloramphenicol (Cm) concentration range from 5 to 100 ug/ml.

For each of the positive colonies, molecular evolution was performed using two-step mutagenesis PCR (error-prone PCR) and a DNA shuffling technique. Specifically, the mutagenesis PCR was performed using pKD-SepRS-EFTu as a template together with a forward primer (SEQ ID NO 34: SP263F, 5'-CAA TTT GGC TTT ACA AAC TTT GAA TTC ATT CCT GAT GAA AAG-3') and a reverse primer (SEQ ID NO: 35: EF67R, 5'-AGA AGT GTT GAT GGT GAT AC-3'). The mutagenesis PCR was performed in Taq buffer containing 0.5 nM primer, 0.2 mM dATP and GTP, 1 mM dCTP and dTTP, 0.025 U/ul Taq DNA polymerase, 7 mM MgCl₂ and 0.5 mM MnCl₂. Then, the PCR product was digested with DNaseI, and the resulting 50-150 bp DNA fragments were purified by agarose gel extraction. Then, to perform the DNA shuffling technique, the DNA fragments were reassembled by primerless PCR and amplified by PCR using primers of SEQ ID NOs: 34 and 35. The resulting DNA was treated with the restriction enzymes EcoRI and SacI and ligated with a pKD-SepRS-EFSep67S vector treated with the same restriction enzymes. The resulting vectors were transformed into an *E. coli* Top10ΔserB strain having pCAT112TAG-SepT, followed by the resistance selection technique using the activity of CAT as described above. As a result, about 300 positive colonies were selected after the first-step molecular evolution, and about 100 positive colonies were selected after the second-step molecular evolution. The intracellular aminoacylation activity of the positive colonies was measured using a CAT assay technique. As a result, SepRS9 showed the highest activity (see lane 4 in FIG. 1).

FIG. 2 summarizes the amino acid sequences of the SepRS mutants selected by molecular evolution. The SepRS mutant having the highest activity has an amino acid sequence of SEQ ID NO: 1, and a gene encoding the SepRS mutant has a nucleotide sequence of SEQ ID NO: 5.

(2) Construction of EF-Tu Mutants

Figure 3:
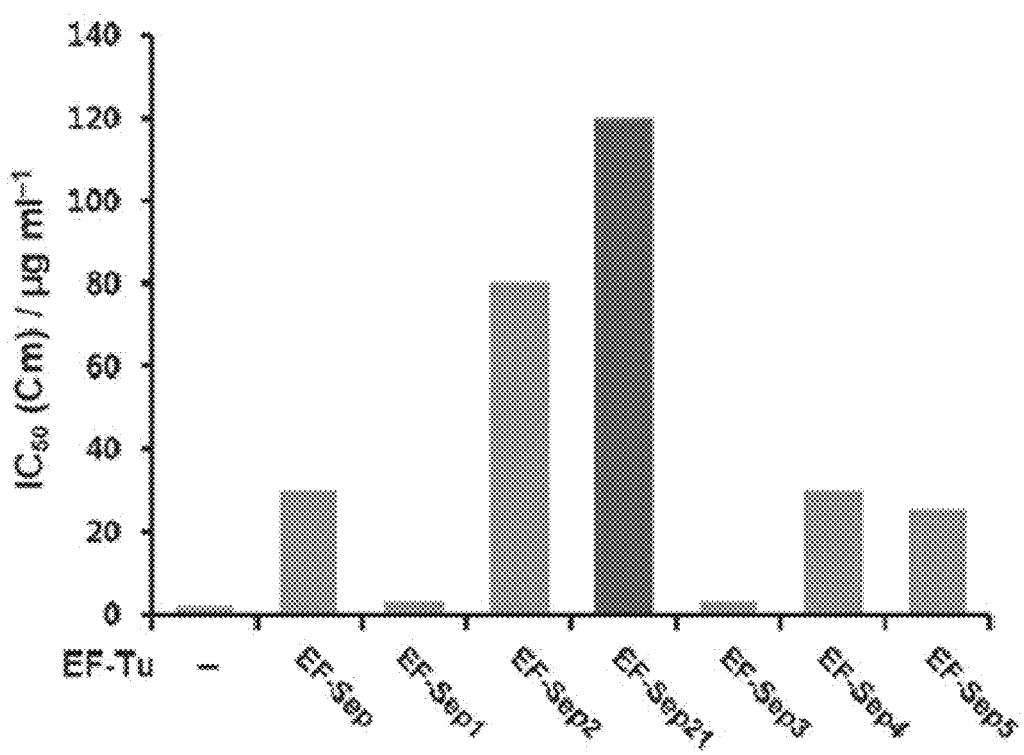
FIG. 3 shows the chloramphenicol resistance (IC 50, ug/ml) of an *E. coli* strain that includes an amber stop codon (UAG) inserted into the 112$^{th}$ amino acid (asp) position of chloramphenicol acetyltransferase (CAT) and that has tRNA$^{Sep}$ and a combination of EF-Tu mutants (EF-Sep1, EF-Sep2, EF-Sep21, EF-Sep3, EF-Sep4, and EF-Sep5) expressed together with SepRS. The *E. coli* strain was *E. coli* Top10ΔserB, and the selection process was performed on an LB plate medium having mM phosphoserine (Sep) and various concentrations of chloramphenicol.

To further improve the binding activity of EF-Tu mutants, a site-specific mutation technique was performed in which each of the mutated amino acids (H (histidine)-to-R (arginine) substitution at amino acid position 67, E (glutamic acid)-to-N(asparagines) substitution at amino acid position 216, D (aspartic acid)-to-G (glycine) substitution at amino acid position 217, F (phenylalanine)-to-Y (tyrosine) substitution at amino acid position 219, T (threonine)-to-S (serine) substitution at amino acid position 229, and N (asparagines)-to-W (tryptophan) at amino acid position 274) of the amino acid sequence of an EF-Tu mutant (EF-Sep) was individually mutated to alanine (Ala). For this purpose, PCR was performed using the following primer combination, thereby constructing primary EF-Tu mutants:

SEQ ID NO: 36:
EF67AN, 5'-GTA TCA CCA TCA ACA CTT CTG CGG TTG AAT ACG ACA CCC CG-3';

SEQ ID NO: 37:
EF67C, 5'-AGA AGT GTT GAT GGT GAT AC-3';

SEQ ID NO: 38:
EF216AN, 5'-CCG TTC CTG CTG CCG ATC GCG GGG GTA TAC TCC ATC TCC-3';

SEQ ID NO: 39:
EF216C, 5'-GAT CGG CAG CAG GAA CGG-3';

SEQ ID NO: 40:
EF219AN, 5'-CTG CCG ATC AAC GGG GTA GCG TCC ATC TCC GGT CGT GGT-3';

SEQ ID NO: 41:
EF219C, 5'-TAC CCC GTT GAT CGG CAG-3';

SEQ ID NO: 42:
EF229AN, 5'-GGT CGT GGT ACC GTT GTT GCG GGT CGT GTA GAA CGC GG-3';

SEQ ID NO: 43:
EF229C, 5'-AAC AAC GGT ACC ACG ACC-3';

SEQ ID NO: 44:
EF274AN, 5'-GAA GGC CGT GCT GGT GAG GCG GTA GGT GTT CTG CTG CG-3';

SEQ ID NO: 45:
EF274C, 5'-CTC ACC AGC ACG GCC TTC-3';

Each of the resulting EF-Tu mutants, including EF-Sep1 (R67A), EF-Sep2 (N216A), EF-Sep3 (Y219A), EF-Sep4 (S229A), and EF-Sep5 (W274A) was transformed into an *E. coli* Top10ΔserB strain having pCAT112TAG-SepT, and the intracellular aminoacylation activity of the mutants was measured using the CAT assay technique as described above. As a result, it was shown that the EF-Sep2 mutant had the highest activity (see FIG. 3). Thus, PCR for randomly mutating the 216th amino acid was performed using pKD-SepRS-EFSep216A as a template together with a forward primer (SEQ ID NO 46: E216XN, 5'-CCG TTC CTG CTG CCG ATC NNS GGG GTA TAC TCC ATC TCC-3') and a reverse primer (SEQ ID NO 47: E216C, 5'-GAT CGG CAG CAG GAA CGG-3') (Park H-S et al., *Science* 2006, 311:535-538).

Figure 4:
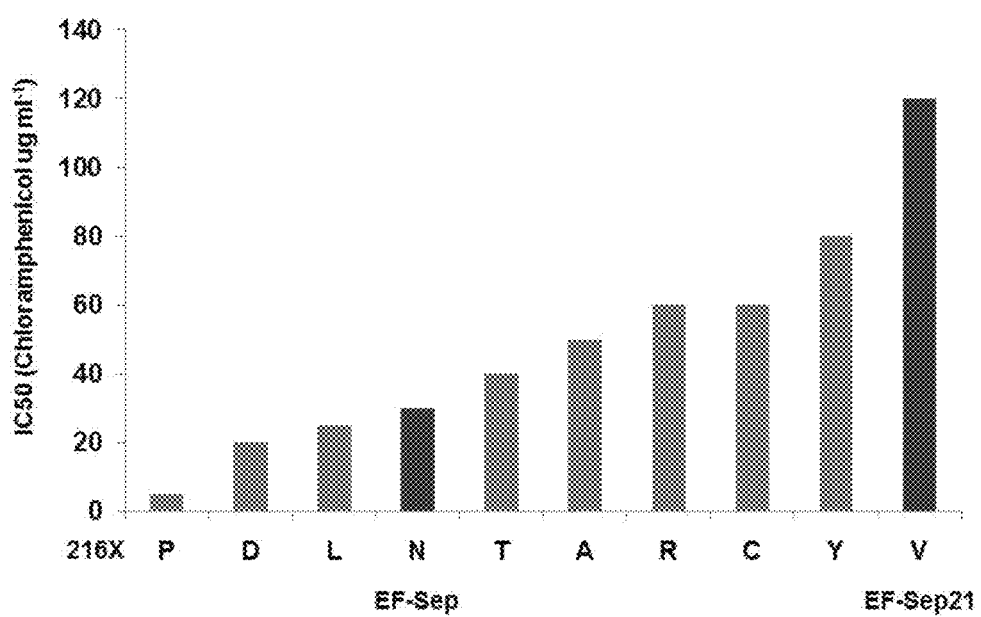
FIG. 4 shows the amino acid sequence of EF-Tu mutants, selected by a molecular evolution technique, and the chloramphenicol resistance-based acetyltransferase activity of each of the mutants.

The resulting PCR products were purified by agarose gel extraction, after which they were treated with the restriction enzymes EcoRI and SalI and ligated with a pKD-SepRS-EFSep21A vector treated with the same restriction enzymes, thereby obtaining pKD-SepRS-EFSep216X recombinant vectors. Then, the recombinant vectors were transformed into an *E. coli* Top10ΔserB strain having pCAT112TAG-SepT, and the *E. coli* cells were cultured on an LB plate medium containing 0-160 μg/ml of chloramphenicol, 50 μg/ml of kanamycin, 10 μg/ml of tetracycline and 0.05 mM IPTG (isopropyl-β-D-thiogalactopyranoside) at 30° C. for 60 hours, thereby obtaining about 500 positive colonies. Among these colonies, 20 colonies having resistance to 20 ug/ml of chloramphenicol were selected and sequenced. As a result, it could be seen that the colonies were mutants in which the 216th amino acid was substituted with one of arginine, valine, aspartic acid, cysteine, threonine, tyrosine, alanine, leucine and proline. Among the mutants, the EF-Sep21 mutant (having an E (glutamic acid)-to-valine (V) substitution at amino acid position 216) had the highest intracellular aminoacylation activity (see lane 5 in FIG. 3, and FIG. 4).

Among the EF-Tu mutants selected by molecular evolution, the mutant having the highest activity has an amino acid sequence of SEQ ID NO: 6, and a gene encoding the mutant has a nucleotide sequence of SEQ ID NO: 15.

Example 2

Figure 5:
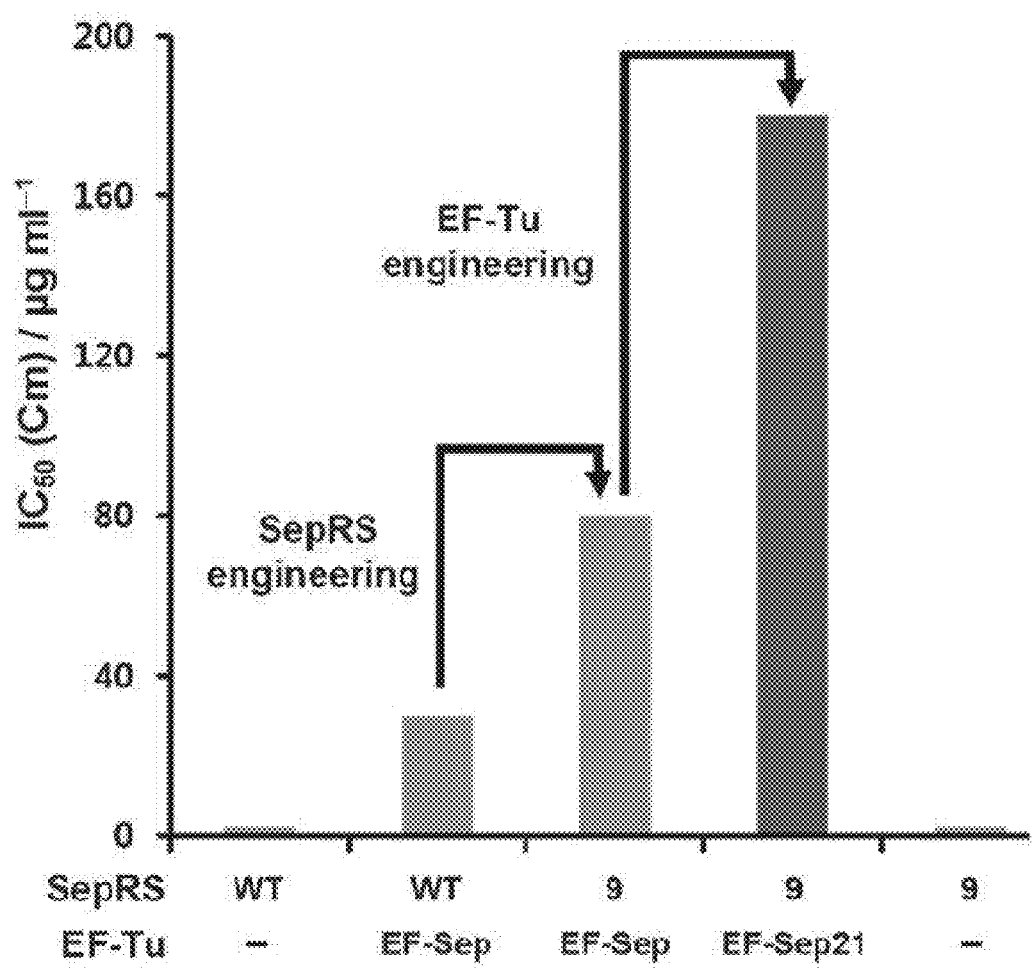
FIG. 5 shows the chloramphenicol resistance (IC 50, ug/ml) of an *E. coli* strain that includes an amber stop codon (UAG) inserted into the 112$^{th}$ amino acid (asp) position of chloramphenicol acetyltransferase (CAT) and that has tRNA$^{Sep}$ and a combination of SepRS mutants (SepRS6 or SepRS9) and an EF-Tu mutant (EF-Sep21). The *E. coli* strain was *E. coli* Top10ΔserB, and the selection process was performed on an LB plate medium having 2 mM phosphoserine (Sep) and various concentrations of chloramphenicol.

Verification of Intracellular Sep-Incorporating Activity of SepRS and EF-Tu Mutants Each of the vectors pKD-SepRS, pKD-SepRS-EFSep, pKD-SepRS9-EFSep, pKD-SepRS-EFSep21 and pKD-SepRS9 was transformed into an *E. coli* Top10ΔserB strain having pCAT112TAG-SepT, and the intracellular aminoacylation activity of the vectors was measured using the CAT assay technique as described above. As a result, it was shown that the vector comprising both the SepRS9 and EF-Sep21 mutants constructed in the present invention had the highest intracellular Sep-incorporating activity (see lane 4 in FIG. 5).

Example 3

Protein Production Ability of SepRS and EF-Tu Mutants Verified by Purification of Phosphorylated Histone H3

The *Xenopus laevis* histone H3 gene having a His6-tag and a TEV protease recognition sequence at the N-terminus was cloned between the BamHI and AscI sites of a PCDFDuet vector (Novagen) to make pCDFDuet-H3 wt. Then, serine at amino acid position 10 of the gene was substituted with an amber stop codon (UAG) to construct a pCDFDuet-H3S10TAG vector. In addition, the recombinant vector pETDuet-SepRS9-SepT having tRNA$^{Sep}$ inserted between the NotI and BglII sites of pETDuet(Novagen) and SepRS9 inserted between the NcoI and SacI sites was constructed using the following primers:

```
SEQ ID NO: 48:
DuetF, 5'-GGG ATC TCG ACG CTC TCC C-3';

SEQ ID NO: 49:
DuetSepTR, 5'-CCC CTA GAC TAC CCC GGC TTT

AAC TAA TAT ACT AAG ATG-3';

SEQ ID NO: 50:
SepTF, 5'-GCC GGG GTA GTC TAG GGG-3';

SEQ ID NO: 51:
SepTBglR, 5'-TGC CTG AAC TAG ATC TTG GAG

CCG GGG GTG GGA T-3'.
```

Figure 6:
FIG. 6 is a photograph showing the results of electrophoresis and Western blot analysis (performed using the corresponding antibody) of a mutant (H3S10ph), derived from *Xenopus laevis* in an *E. coli* BL21(DE3) strain and having a serine codon-to-UAG replacement at the 10$^{th}$ amino acid position of the N-terminus of histone H3.

In order to express the histone H3 phosphorylated at the 10$^{th}$ amino acid position, each of the pKD-SepRS9-EFSep21, pETDuet-SepRS9-sepT and pCDFDuet-H3S10TAG vectors was inserted into an *E. coli* BL21(DE3) strain. The strain was cultured in 2xYT medium containing 50 μg/ml Kan, 100 μg/ml ampicillin (Amp) and 50 μg/ml streptomycin (Sm) for 18 hours, after it was inoculated into 1 L of 2xYT medium and further cultured at 30° C. until an absorbance (OD) of 0.5 was reached. 0.5 mM IPTG was added to the culture medium which was then incubated at 37° C. for 12 hours to induce the expression of H3S10ph. The strain was centrifuged from the medium, and then suspended in 50 ml of lysis buffer (6 M guanidinium chloride, 100 mM NaH$_2$PO$_4$ (pH 8.0), 10 mM Tris-HCl, and 3 mM β-mercaptoethanol). The suspension was centrifuged, and the supernatant was loaded into a 0.5 ml Ni$^{2+}$-NTA agarose column. The column was washed with washing buffer (8M urea, 100 mM NaH$_2$PO$_4$ (pH 6.3), 10 mM Tris-HCl and 3 mM β-mercaptoethanol), and then protein was isolated from the column using elution buffer (8M urea, 100 mM NaH$_2$PO$_4$ (pH 4.5), 10 mM Tris-HCl, and 3 mM β-mercaptoethanol). The isolated protein was dialyzed with distilled water containing 3 mM β-mercaptoethanol at 4° C., followed by lyophilization. The resulting H3S10ph protein having a His. tag and a TEV protease recognition sequence at the N-terminus had an amino acid sequence of SEQ ID NO: 52. When the protein was produced using the SepRS9 and EF-Sep21 mutants constructed in the present invention, the production amount of the protein greatly increased from a level of 25 ug (MEK1) per liter to a level of 3 mg per liter (see lane 4 in FIG. 6).

Example 4

Influence of Phosphorylation of Histone H3S10 on Acetylation of Lysine Residues at N-Terminus of Histone H3

(1) Histone Octamer Assembly and Nucleosomal Array Reconstitution

To construct various chromatin substrates, a histone octamer was assembled. Lyophilized histones (H4, H2A, H2B, and H3 wt or H3S10ph) were added to unfolding buffer (7M guanidinium chloride, 20 mM Tris-HCl (pH7.5), and 10 mM DTT) and incubated with stirring at room temperature for 3 hours. Then, the histones were dialyzed three times in refolding buffer (2M NaCl, 10 mM Tris-HCl (pH8.0), 1 mM EDTA, and 5 mM β-mercaptoethanol) at 4° C. The resulting octamer was separated by centrifugation in a glycerol concentration gradient (K. Luger, T. J. et al, *Methods Enzymol* 1999, 304, 3.). Reconstitution of a nucleosomal array was performed by incubating 35 pg of a DNA template (pGEM-3z/601 or pG5E4T) with the histone octamer (1:1.1 mass ratio) in NaCl buffer while reducing the concentration gradient from 2M to 0.1M (D. J. Steger, et al., *Proc Natl Acad Sci USA*, 1998, 95, 12924, M. Vignali, et al., *EMBO J* 2000, 19, 2629). The nucleosomal array was separated by centrifugation in a glycerol concentration gradient and electrophoresed on 0.8% agarose gel.

(2) Measurement of Histone Acetyltransferase (HAT) Activity

*Saccharomyces cerevisiae* GCN5 with His6-tag was expressed in an *E. coli* BL21(DE3) strain and purified using a Ni$^{2+}$-NTA agarose column. A Spt-Ada-Gcn5-acetyltransferase complex (SAGA) was purified by tandem affinity purification (TAP) (O. Puig, et al., *Methods* 2001, 24, 218).

In order to measure HAT activity, 60 pmol of each of histone H3, the histone octamer and the nucleosomal array was incubated with 0.6 pmol of recombinant Gcn5 protein or 0.3 pmol of the SAGA complex in HAT buffer (50 mM Tris-HCl (pH7.5), 5% glycerol, 0.125 mM EDTA, 50 mM KCl, 1 mM DTT, 1 mM PMSF, 10 mM sodium butyrate, 2.5 μM $^{[3H]}$Acetyl-CoA (3.3 Ci/mmol), 1 mM Na$_3$.Vo$_4$, and 5 mM NaF) at 30° C. (M. A. Shogren-Knaak, et al., *J Biol Chem* 2003, 278, 15744.).

The reaction solution was transferred to P81 filter paper (Whatman) to stop the reaction, and then washed four times with 50 mM NaHCO$_3$/Na$_2$CO$_3$. (pH 8.5) and immersed in acetone. Next, the HAT activity was measured using a scintillation counter.

Figure 7:
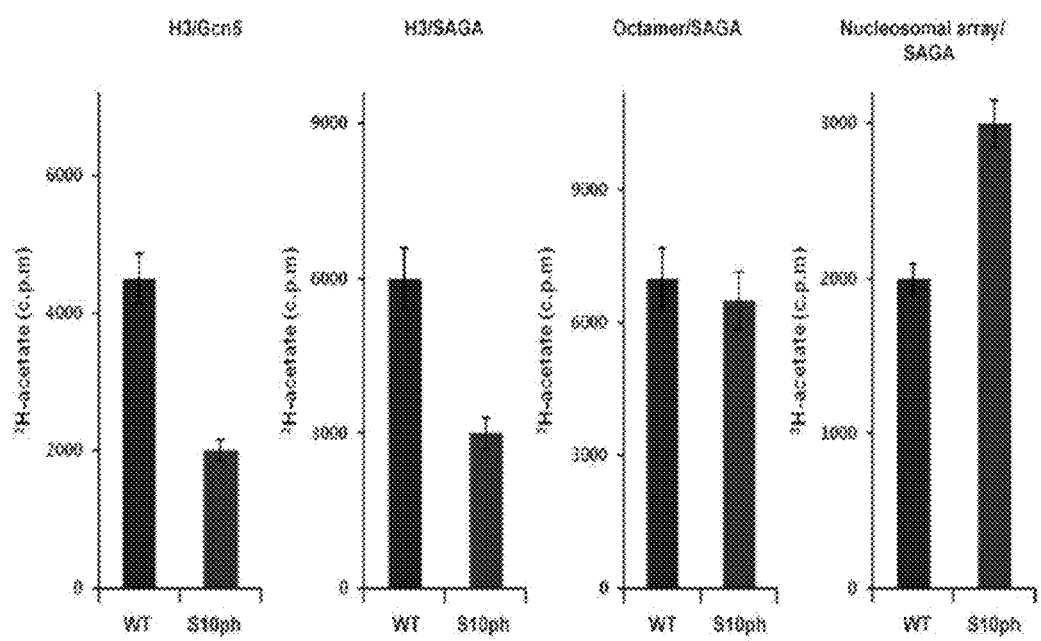
FIG. 7 is a graphic diagram showing the results of measuring the histone acetyltransferase (HAT) activity of SAGA and Gcn5 using various chromatin substrates. A combination of the chromatin substrate with SAGA or Gcn5 follows the descriptions above the graphs.

As a result, unlike previous reports (M. A. Shogren-Knaak, et al., *J. Biol. Chem.* 2003, 278, 15744), it was shown that the phosphorylation of histone H3S10 in the nucleosomal array state promoted the SAGA complex-mediated acetylation of histone H3 (see FIG. 7).

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method of producing a phosphorylated protein by incorporating phosphoserine into the specific position of a target protein or polypeptide, the method comprising expressing an mRNA encoding the target protein in the system using tRNA$^{Sep}$ serving to recognize at least one codon in the mRNA of the target protein or polypeptide, a SepRS mutant serving to aminoacylate tRNA$^{Sep}$ with phosphoserine (Sep), a EF-Tu mutant serving to bind and deliver Sep-tRNA$^{Sep}$ to the ribosome, and the ribosome incorporating the Sep into the specific target protein or polypeptide recognized by the Sep-tRNA$^{sep}$, wherein the SepRS mutant has at least one mutation selected from the group consisting of: K347E, N352D, E412S, E412D, E414I, E414M, E414W, F452L, E481D, P495R, P495S, I496R, I496S, L512I, and V532A in an O-phosphoseryl-tRNA synthetase (SepRS) having the amino acid sequence of SEQ ID NO:17, and wherein EF-Tu mutant has at least one mutation selected from the group consisting of: H67R, E216V, E216L, E216T, E216A, E216R, E216C, E216Y, D217G, F219Y, T229S, T229A, W274A, and W274N in an EF-Tu having the amino acid sequence of SEQ ID NO:19.

2. The method of claim 1, wherein the EF-Tu mutant has an amino acid sequence of any one of SEQ ID NOs: 6 to 14.

3. The SepRS mutant of claim 1, wherein the SepRS mutant has an amino acid sequence of any one of SEQ ID NOs: 1 to 4.

4. The method of claim 1, wherein the tRNA$^{Sep}$ is derived from *Methanocaldococcus jannaschii*.

5. The method of claim 4, wherein the gene encoding the tRNA$^{Sep}$ has a nucleotide sequence set forth in SEQ ID NO: 16.

* * * * *

SEQUENCE LISTING

```
<160> NUMBER OF SEQ ID NOS: 52

<210> SEQ ID NO 1
<211> LENGTH: 537
<212> TYPE: PRT
<213> ORGANISM: Artificial Sequence
<220> FEATURE:
<223> OTHER INFORMATION: synthesized sequence (Mmp SepRS 9)

<400> SEQUENCE: 1

Met Phe Lys Arg Glu Glu Ile Ile Glu Met Ala Asn Lys Asp Phe Glu
1               5                   10                  15

Lys Ala Trp Ile Glu Thr Lys Asp Leu Ile Lys Ala Lys Lys Ile Asn
            20                  25                  30

Glu Ser Tyr Pro Arg Ile Lys Pro Val Phe Gly Lys Thr His Pro Val
        35                  40                  45

Asn Asp Thr Ile Glu Asn Leu Arg Gln Ala Tyr Leu Arg Met Gly Phe
    50                  55                  60

Glu Glu Tyr Ile Asn Pro Val Ile Val Asp Glu Arg Asp Ile Tyr Lys
65                  70                  75                  80

Gln Phe Gly Pro Glu Ala Met Ala Val Leu Asp Arg Cys Phe Tyr Leu
                85                  90                  95

Ala Gly Leu Pro Arg Pro Asp Val Gly Leu Ser Asp Glu Lys Ile Ser
            100                 105                 110

Gln Ile Glu Lys Leu Gly Ile Lys Val Ser Glu His Lys Glu Ser Leu
        115                 120                 125

Gln Lys Ile Leu His Gly Tyr Lys Lys Gly Thr Leu Asp Gly Asp Asp
    130                 135                 140

Leu Val Leu Glu Ile Ser Asn Ala Leu Glu Ile Ser Ser Glu Met Gly
145                 150                 155                 160

Leu Lys Ile Leu Glu Asp Val Phe Pro Glu Phe Lys Asp Leu Thr Ala
                165                 170                 175

Val Ser Ser Lys Leu Thr Leu Arg Ser His Met Thr Ser Gly Trp Phe
            180                 185                 190

Leu Thr Val Ser Asp Leu Met Asn Lys Lys Pro Leu Pro Phe Lys Leu
        195                 200                 205

Phe Ser Ile Asp Arg Cys Phe Arg Arg Glu Gln Lys Glu Asp Lys Ser
    210                 215                 220

His Leu Met Thr Tyr His Ser Ala Ser Cys Ala Ile Ala Gly Glu Gly
225                 230                 235                 240

Val Asp Ile Asn Asp Gly Lys Ala Ile Ala Glu Gly Leu Leu Ser Gln
                245                 250                 255

Phe Gly Phe Thr Asn Phe Glu Phe Ile Pro Asp Glu Lys Lys Ser Lys
            260                 265                 270

Tyr Tyr Thr Pro Glu Thr Gln Thr Glu Val Tyr Ala Tyr His Pro Lys
        275                 280                 285

Leu Lys Glu Trp Leu Glu Val Ala Thr Phe Gly Val Tyr Ser Pro Val
    290                 295                 300
```

```
Ala Leu Ser Lys Tyr Gly Ile Asp Val Pro Val Met Asn Leu Gly Leu
305                 310                 315                 320

Gly Val Glu Arg Leu Ala Met Ile Ser Gly Asn Phe Ala Asp Val Arg
            325                 330                 335

Glu Met Val Tyr Pro Gln Phe Tyr Glu His Glu Leu Asn Asp Arg Asp
                340                 345                 350

Val Ala Ser Met Val Lys Leu Asp Lys Val Pro Val Met Asp Glu Ile
            355                 360                 365

Tyr Asp Leu Thr Lys Glu Leu Ile Glu Ser Cys Val Lys Asn Lys Asp
        370                 375                 380

Leu Lys Ser Pro Cys Glu Leu Ala Ile Glu Lys Thr Phe Ser Phe Gly
385                 390                 395                 400

Lys Thr Lys Lys Asn Val Lys Ile Asn Ile Phe Ser Lys Ile Glu Gly
                405                 410                 415

Lys Asn Leu Leu Gly Pro Ser Ile Leu Asn Glu Ile Tyr Val Tyr Asp
            420                 425                 430

Gly Asn Val Ile Gly Ile Pro Glu Ser Phe Asp Gly Val Lys Glu Glu
            435                 440                 445

Phe Lys Asp Phe Leu Glu Lys Gly Lys Ser Glu Gly Val Ala Thr Gly
        450                 455                 460

Ile Arg Tyr Ile Asp Ala Leu Cys Phe Lys Ile Thr Ser Lys Leu Glu
465                 470                 475                 480

Glu Ala Phe Val Ser Asn Thr Thr Glu Phe Lys Val Lys Val Arg Arg
                485                 490                 495

Val Arg Ser Leu Ser Asp Ile Asn Leu Lys Ile Asp Asp Ile Ala Ile
            500                 505                 510

Lys Gln Ile Met Ser Lys Asn Lys Val Ile Asp Val Arg Gly Pro Val
        515                 520                 525

Phe Leu Asn Val Glu Val Lys Ile Glu
        530                 535

<210> SEQ ID NO 2
<211> LENGTH: 537
<212> TYPE: PRT
<213> ORGANISM: Artificial Sequence
<220> FEATURE:
<223> OTHER INFORMATION: synthesized sequence (Mmp SepRS 10)

<400> SEQUENCE: 2

Met Phe Lys Arg Glu Glu Ile Ile Glu Met Ala Asn Lys Asp Phe Glu
1               5                   10                  15

Lys Ala Trp Ile Glu Thr Lys Asp Leu Ile Lys Ala Lys Lys Ile Asn
            20                  25                  30

Glu Ser Tyr Pro Arg Ile Lys Pro Val Phe Gly Lys Thr His Pro Val
        35                  40                  45

Asn Asp Thr Ile Glu Asn Leu Arg Gln Ala Tyr Leu Arg Met Gly Phe
    50                  55                  60

Glu Glu Tyr Ile Asn Pro Val Ile Val Asp Glu Arg Asp Ile Tyr Lys
65                  70                  75                  80

Gln Phe Gly Pro Glu Ala Met Ala Val Leu Asp Arg Cys Phe Tyr Leu
                85                  90                  95

Ala Gly Leu Pro Arg Pro Asp Val Gly Leu Ser Asp Glu Lys Ile Ser
            100                 105                 110

Gln Ile Glu Lys Leu Gly Ile Lys Val Ser Glu His Lys Glu Ser Leu
        115                 120                 125
```

```
Gln Lys Ile Leu His Gly Tyr Lys Lys Gly Thr Leu Asp Gly Asp
    130                 135                 140
Leu Val Leu Glu Ile Ser Asn Ala Leu Glu Ile Ser Ser Glu Met Gly
145                 150                 155                 160
Leu Lys Ile Leu Glu Asp Val Phe Pro Glu Phe Lys Asp Leu Thr Ala
                165                 170                 175
Val Ser Ser Lys Leu Thr Leu Arg Ser His Met Thr Ser Gly Trp Phe
                180                 185                 190
Leu Thr Val Ser Asp Leu Met Asn Lys Lys Pro Leu Pro Phe Lys Leu
            195                 200                 205
Phe Ser Ile Asp Arg Cys Phe Arg Arg Glu Gln Lys Glu Asp Lys Ser
    210                 215                 220
His Leu Met Thr Tyr His Ser Ala Ser Cys Ala Ile Ala Gly Glu Gly
225                 230                 235                 240
Val Asp Ile Asn Asp Gly Lys Ala Ile Ala Glu Gly Leu Leu Ser Gln
                245                 250                 255
Phe Gly Phe Thr Asn Phe Glu Phe Ile Pro Asp Glu Lys Lys Ser Lys
                260                 265                 270
Tyr Tyr Thr Pro Glu Thr Gln Thr Glu Val Tyr Ala Tyr His Pro Lys
            275                 280                 285
Leu Lys Glu Trp Leu Glu Val Ala Thr Phe Gly Val Tyr Ser Pro Val
    290                 295                 300
Ala Leu Ser Lys Tyr Gly Ile Asp Val Pro Val Met Asn Leu Gly Leu
305                 310                 315                 320
Gly Val Glu Arg Leu Ala Met Ile Ser Gly Asn Phe Ala Asp Val Arg
                325                 330                 335
Glu Met Val Tyr Pro Gln Phe Tyr His Lys Leu Asn Asp Arg Asn
                340                 345                 350
Val Ala Ser Met Val Lys Leu Asp Lys Val Pro Val Met Asp Glu Ile
            355                 360                 365
Tyr Asp Leu Thr Lys Glu Leu Ile Glu Ser Cys Val Lys Asn Lys Asp
    370                 375                 380
Leu Lys Ser Pro Cys Glu Leu Ala Ile Glu Lys Thr Phe Ser Phe Gly
385                 390                 395                 400
Lys Thr Lys Lys Asn Val Lys Ile Asn Ile Phe Ser Lys Met Glu Gly
                405                 410                 415
Lys Asn Leu Leu Gly Pro Ser Ile Leu Asn Glu Ile Tyr Val Tyr Asp
            420                 425                 430
Gly Asn Val Ile Gly Ile Pro Glu Ser Phe Asp Gly Val Lys Glu Glu
        435                 440                 445
Phe Lys Asp Leu Leu Glu Lys Gly Lys Ser Glu Gly Val Ala Thr Gly
    450                 455                 460
Ile Arg Tyr Ile Asp Ala Leu Cys Phe Lys Ile Thr Ser Lys Leu Glu
465                 470                 475                 480
Glu Ala Phe Val Ser Asn Thr Thr Glu Phe Lys Val Lys Val Arg Ser
                485                 490                 495
Val Arg Ser Leu Ser Asp Ile Asn Leu Lys Ile Asp Asp Ile Ala Leu
            500                 505                 510
Lys Gln Ile Met Ser Lys Asn Lys Val Ile Asp Val Arg Gly Pro Val
        515                 520                 525
Phe Leu Asn Val Glu Val Lys Ile Glu
    530                 535
```

<210> SEQ ID NO 3
<211> LENGTH: 537
<212> TYPE: PRT
<213> ORGANISM: Artificial Sequence
<220> FEATURE:
<223> OTHER INFORMATION: synthesized sequence (Mmp SepRS 11)

<400> SEQUENCE: 3

```
Met Phe Lys Arg Glu Glu Ile Ile Glu Met Ala Asn Lys Asp Phe Glu
1               5                   10                  15

Lys Ala Trp Ile Glu Thr Lys Asp Leu Ile Lys Ala Lys Lys Ile Asn
            20                  25                  30

Glu Ser Tyr Pro Arg Ile Lys Pro Val Phe Gly Lys Thr His Pro Val
        35                  40                  45

Asn Asp Thr Ile Glu Asn Leu Arg Gln Ala Tyr Leu Arg Met Gly Phe
    50                  55                  60

Glu Glu Tyr Ile Asn Pro Val Ile Val Asp Glu Arg Asp Ile Tyr Lys
65                  70                  75                  80

Gln Phe Gly Pro Glu Ala Met Ala Val Leu Asp Arg Cys Phe Tyr Leu
                85                  90                  95

Ala Gly Leu Pro Arg Pro Asp Val Gly Leu Ser Asp Glu Lys Ile Ser
            100                 105                 110

Gln Ile Glu Lys Leu Gly Ile Lys Val Ser Glu His Lys Glu Ser Leu
        115                 120                 125

Gln Lys Ile Leu His Gly Tyr Lys Lys Gly Thr Leu Asp Gly Asp Asp
    130                 135                 140

Leu Val Leu Glu Ile Ser Asn Ala Leu Glu Ile Ser Ser Glu Met Gly
145                 150                 155                 160

Leu Lys Ile Leu Glu Asp Val Phe Pro Glu Phe Lys Asp Leu Thr Ala
                165                 170                 175

Val Ser Ser Lys Leu Thr Leu Arg Ser His Met Thr Ser Gly Trp Phe
            180                 185                 190

Leu Thr Val Ser Asp Leu Met Asn Lys Lys Pro Leu Pro Phe Lys Leu
        195                 200                 205

Phe Ser Ile Asp Arg Cys Phe Arg Arg Glu Gln Lys Glu Asp Lys Ser
    210                 215                 220

His Leu Met Thr Tyr His Ser Ala Ser Cys Ala Ile Ala Gly Glu Gly
225                 230                 235                 240

Val Asp Ile Asn Asp Gly Lys Ala Ile Ala Glu Gly Leu Leu Ser Gln
                245                 250                 255

Phe Gly Phe Thr Asn Phe Glu Phe Ile Pro Asp Glu Lys Lys Ser Lys
            260                 265                 270

Tyr Tyr Thr Pro Glu Thr Gln Thr Glu Val Tyr Ala Tyr His Pro Lys
        275                 280                 285

Leu Lys Glu Trp Leu Glu Val Ala Thr Phe Gly Val Tyr Ser Pro Val
    290                 295                 300

Ala Leu Ser Lys Tyr Gly Ile Asp Val Pro Val Met Asn Leu Gly Leu
305                 310                 315                 320

Gly Val Glu Arg Leu Ala Met Ile Ser Gly Asn Phe Ala Asp Val Arg
                325                 330                 335

Glu Met Val Tyr Pro Gln Phe Tyr Glu His Lys Leu Asn Asp Arg Asn
            340                 345                 350

Val Ala Ser Met Val Lys Leu Asp Lys Val Pro Val Met Asp Glu Ile
        355                 360                 365
```

-continued

```
Tyr Asp Leu Thr Lys Glu Leu Ile Glu Ser Cys Val Lys Asn Lys Asp
    370                 375                 380

Leu Lys Ser Pro Cys Glu Leu Ala Ile Glu Lys Thr Phe Ser Phe Gly
385                 390                 395                 400

Lys Thr Lys Lys Asn Val Lys Ile Asn Ile Phe Asp Lys Trp Glu Gly
                405                 410                 415

Lys Asn Leu Leu Gly Pro Ser Ile Leu Asn Glu Ile Tyr Val Tyr Asp
                420                 425                 430

Gly Asn Val Ile Gly Ile Pro Glu Ser Phe Asp Gly Val Lys Glu Glu
                435                 440                 445

Phe Lys Asp Phe Leu Glu Lys Gly Lys Ser Gly Val Ala Thr Gly
450                 455                 460

Ile Arg Tyr Ile Asp Ala Leu Cys Phe Lys Ile Thr Ser Lys Leu Glu
465                 470                 475                 480

Asp Ala Phe Val Ser Asn Thr Thr Glu Phe Lys Val Lys Val Arg Ser
                485                 490                 495

Val Arg Ser Leu Ser Asp Ile Asn Leu Lys Ile Asp Asp Ile Ala Leu
                500                 505                 510

Lys Gln Ile Met Ser Lys Asn Lys Val Ile Asp Val Arg Gly Pro Val
                515                 520                 525

Phe Leu Asn Ala Glu Val Lys Ile Glu
                530                 535

<210> SEQ ID NO 4
<211> LENGTH: 537
<212> TYPE: PRT
<213> ORGANISM: Artificial Sequence
<220> FEATURE:
<223> OTHER INFORMATION: synthesized sequence (Mmp SepRS 6)

<400> SEQUENCE: 4

Met Phe Lys Arg Glu Glu Ile Ile Glu Met Ala Asn Lys Asp Phe Glu
1               5                   10                  15

Lys Ala Trp Ile Glu Thr Lys Asp Leu Ile Lys Ala Lys Lys Ile Asn
                20                  25                  30

Glu Ser Tyr Pro Arg Ile Lys Pro Val Phe Gly Lys Thr His Pro Val
            35                  40                  45

Asn Asp Thr Ile Glu Asn Leu Arg Gln Ala Tyr Leu Arg Met Gly Phe
        50                  55                  60

Glu Glu Tyr Ile Asn Pro Val Ile Val Asp Glu Arg Asp Ile Tyr Lys
65                  70                  75                  80

Gln Phe Gly Pro Glu Ala Met Ala Val Leu Asp Arg Cys Phe Tyr Leu
                85                  90                  95

Ala Gly Leu Pro Arg Pro Asp Val Gly Leu Ser Asp Glu Lys Ile Ser
            100                 105                 110

Gln Ile Glu Lys Leu Gly Ile Lys Val Ser Glu His Lys Glu Ser Leu
        115                 120                 125

Gln Lys Ile Leu His Gly Tyr Lys Lys Gly Thr Leu Asp Gly Asp Asp
    130                 135                 140

Leu Val Leu Glu Ile Ser Asn Ala Leu Glu Ile Ser Ser Glu Met Gly
145                 150                 155                 160

Leu Lys Ile Leu Glu Asp Val Phe Pro Glu Phe Lys Asp Leu Thr Ala
                165                 170                 175

Val Ser Ser Lys Leu Thr Leu Arg Ser His Met Thr Ser Gly Trp Phe
            180                 185                 190
```

```
Leu Thr Val Ser Asp Leu Met Asn Lys Lys Pro Leu Pro Phe Lys Leu
            195                 200                 205

Phe Ser Ile Asp Arg Cys Phe Arg Arg Glu Gln Lys Glu Asp Lys Ser
210                 215                 220

His Leu Met Thr Tyr His Ser Ala Ser Cys Ala Ile Ala Gly Glu Gly
225                 230                 235                 240

Val Asp Ile Asn Asp Gly Lys Ala Ile Ala Glu Gly Leu Leu Ser Gln
                245                 250                 255

Phe Gly Phe Thr Asn Phe Glu Phe Ile Pro Asp Glu Lys Lys Ser Lys
            260                 265                 270

Tyr Tyr Thr Pro Glu Thr Gln Thr Glu Val Tyr Ala Tyr His Pro Lys
        275                 280                 285

Leu Lys Glu Trp Leu Glu Val Ala Thr Phe Gly Val Tyr Ser Pro Val
    290                 295                 300

Ala Leu Ser Lys Tyr Gly Ile Asp Val Pro Val Met Asn Leu Gly Leu
305                 310                 315                 320

Gly Val Glu Arg Leu Ala Met Ile Ser Gly Asn Phe Ala Asp Val Arg
                325                 330                 335

Glu Met Val Tyr Pro Gln Phe Tyr Glu His Lys Leu Asn Asp Arg Asn
            340                 345                 350

Val Ala Ser Met Val Lys Leu Asp Lys Val Pro Val Met Asp Glu Ile
        355                 360                 365

Tyr Asp Leu Thr Lys Glu Leu Ile Glu Ser Cys Val Lys Asn Lys Asp
    370                 375                 380

Leu Lys Ser Pro Cys Glu Leu Ala Ile Glu Lys Thr Phe Ser Phe Gly
385                 390                 395                 400

Lys Thr Lys Lys Asn Val Lys Ile Asn Ile Phe Ser Lys Ile Glu Gly
                405                 410                 415

Lys Asn Leu Leu Gly Pro Ser Ile Leu Asn Glu Ile Tyr Val Tyr Asp
            420                 425                 430

Gly Asn Val Ile Gly Ile Pro Glu Ser Phe Asp Gly Val Lys Glu Glu
        435                 440                 445

Phe Lys Asp Phe Leu Glu Lys Gly Lys Ser Glu Gly Val Ala Thr Gly
    450                 455                 460

Ile Arg Tyr Ile Asp Ala Leu Cys Phe Lys Ile Thr Ser Lys Leu Glu
465                 470                 475                 480

Glu Ala Phe Val Ser Asn Thr Thr Glu Phe Lys Val Lys Val Ser Arg
                485                 490                 495

Val Arg Ser Leu Ser Asp Ile Asn Leu Lys Ile Asp Asp Ile Ala Leu
            500                 505                 510

Lys Gln Ile Met Ser Lys Asn Lys Val Ile Asp Val Arg Gly Pro Val
        515                 520                 525

Phe Leu Asn Val Glu Val Lys Ile Glu
    530                 535

<210> SEQ ID NO 5
<211> LENGTH: 1614
<212> TYPE: DNA
<213> ORGANISM: Artificial Sequence
<220> FEATURE:
<223> OTHER INFORMATION: synthesized sequence (Mmp SepRS 9)

<400> SEQUENCE: 5
atgtttaaaa gagaagaaat cattgaaatg gccaataagg actttgaaaa agcatggatc      60
gaaactaaag accttataaa agctaaaaag ataaacgaaa gttacccaag aataaaacca     120
```

```
gttttttggaa aaacacaccc tgtaaatgac actattgaaa atttaagaca ggcatatctt    180
agaatgggtt tgaagaata  tataaaccca gtaattgtcg atgaaagaga tatttataaa    240
caattcggcc cagaagctat ggcagttttg gatagatgct tttatttagc gggacttcca    300
agacctgacg ttggtttgag cgatgaaaaa atttcacaga ttgaaaaact tggaattaaa    360
gtttctgagc acaaagaaag tttacaaaaa atacttcacg gatacaaaaa aggaactctt    420
gatggtgacg atttagtttt agaaatttca atgcacttg  aaatttcaag cgagatgggt    480
ttaaaaattt tagaagatgt tttcccagaa tttaaggatt taaccgcagt ttcttcaaaa    540
ttaactttaa gaagccacat gacttcagga tggttcctta ctgtttcaga cctcatgaac    600
aaaaaaccct tgccatttaa actctttca  atcgatagat gttttagaag agaacaaaaa    660
gaagataaaa gccacttaat gacataccac tctgcatcct gtgcaattgc aggtgaaggc    720
gtggatatta atgatggaaa agcaattgca gaaggattat tatcccaatt tggctttaca    780
aactttgaat tcattcctga tgaaaagaaa agtaaatact acacccctga aacacagact    840
gaagtttacg cataccaccc aaaattaaaa gaatggctcg aagttgctac atttggagta    900
tattcgccag ttgcattaag caaatacgga atagatgtac ctgtaatgaa tttgggtctt    960
ggtgttgaaa gacttgcaat gatttctgga aatttcgcag atgttcgaga atggtatat    1020
cctcagtttt acgaacacga acttaatgac cgggatgtcg cttcaatggt aaaactcgat   1080
aaagttccag taatggatga aatttacgat ttaacaaaag aattaattga gtcatgtgtt   1140
aaaaacaaag atttaaaatc cccttgtgaa ttagctattg aaaaaacgtt ttcatttgga   1200
aaaaccaaga aaacgtgaaa gatcaacatc ttcagcaaaa tcgagggcaa gaacctgctc   1260
ggaccttcaa ttttaaacga aatctacgtt tacgatggaa atgtaattgg cattcctgaa   1320
agctttgacg gagtaaaaga agaatttaaa gacttcttag aaaaaggaaa atcagaaggg   1380
gtagcaacag gcattcgata tatcgatgcg ctttgcttta aaattacttc aaaattagaa   1440
gaagcatttg tgtcaaacac tactgagttc aaggtcaagg tgcggcgcgt cagaagttta   1500
agcgacatta acttaaaaat cgatgatatc gcaataaaac agatcatgag caaaaataaa   1560
gtaatcgacg ttagaggccc agtctttta  aatgtcgaag taaaaattga ataa          1614
```

<210> SEQ ID NO 6
<211> LENGTH: 394
<212> TYPE: PRT
<213> ORGANISM: Artificial Sequence
<220> FEATURE:
<223> OTHER INFORMATION: synthesized sequence (EF-Sep variant 21)

<400> SEQUENCE: 6

```
Met Ser Lys Glu Lys Phe Glu Arg Thr Lys Pro His Val Asn Val Gly
1               5                  10                  15

Thr Ile Gly His Val Asp His Gly Lys Thr Thr Leu Thr Ala Ala Ile
            20                  25                  30

Thr Thr Val Leu Ala Lys Thr Tyr Gly Gly Ala Ala Arg Ala Phe Asp
        35                  40                  45

Gln Ile Asp Asn Ala Pro Glu Glu Lys Ala Arg Gly Ile Thr Ile Asn
    50                  55                  60

Thr Ser Arg Val Glu Tyr Asp Thr Pro Thr Arg His Tyr Ala His Val
65                  70                  75                  80

Asp Cys Pro Gly His Ala Asp Tyr Val Lys Asn Met Ile Thr Gly Ala
                85                  90                  95
```

```
Ala Gln Met Asp Gly Ala Ile Leu Val Val Ala Ala Thr Asp Gly Pro
            100                 105                 110

Met Pro Gln Thr Arg Glu His Ile Leu Leu Gly Arg Gln Val Gly Val
        115                 120                 125

Pro Tyr Ile Ile Val Phe Leu Asn Lys Cys Asp Met Val Asp Asp Glu
    130                 135                 140

Glu Leu Leu Glu Leu Val Glu Met Glu Val Arg Glu Leu Leu Ser Gln
145                 150                 155                 160

Tyr Asp Phe Pro Gly Asp Asp Thr Pro Ile Val Arg Gly Ser Ala Leu
                165                 170                 175

Lys Ala Leu Glu Gly Asp Ala Glu Trp Glu Ala Lys Ile Leu Glu Leu
            180                 185                 190

Ala Gly Phe Leu Asp Ser Tyr Ile Pro Glu Pro Glu Arg Ala Ile Asp
        195                 200                 205

Lys Pro Phe Leu Leu Pro Ile Val Gly Val Tyr Ser Ile Ser Gly Arg
    210                 215                 220

Gly Thr Val Val Ser Gly Arg Val Glu Arg Gly Ile Ile Lys Val Gly
225                 230                 235                 240

Glu Glu Val Glu Ile Val Gly Ile Lys Glu Thr Gln Lys Ser Thr Cys
                245                 250                 255

Thr Gly Val Glu Met Phe Arg Lys Leu Leu Asp Glu Gly Arg Ala Gly
            260                 265                 270

Glu Trp Val Gly Val Leu Leu Arg Gly Ile Lys Arg Glu Glu Ile Glu
        275                 280                 285

Arg Gly Gln Val Leu Ala Lys Pro Gly Thr Ile Lys Pro His Thr Lys
    290                 295                 300

Phe Glu Ser Glu Val Tyr Ile Leu Ser Lys Asp Glu Gly Gly Arg His
305                 310                 315                 320

Thr Pro Phe Phe Lys Gly Tyr Arg Pro Gln Phe Tyr Phe Arg Thr Thr
                325                 330                 335

Asp Val Thr Gly Thr Ile Glu Leu Pro Glu Gly Val Glu Met Val Met
            340                 345                 350

Pro Gly Asp Asn Ile Lys Met Val Val Thr Leu Ile His Pro Ile Ala
        355                 360                 365

Met Asp Asp Gly Leu Arg Phe Ala Ile Arg Glu Gly Arg Thr Val
    370                 375                 380

Gly Ala Gly Val Val Ala Lys Val Leu Ser
385                 390

<210> SEQ ID NO 7
<211> LENGTH: 394
<212> TYPE: PRT
<213> ORGANISM: Artificial Sequence
<220> FEATURE:
<223> OTHER INFORMATION: synthesized sequence (EF-Sep variant 2)

<400> SEQUENCE: 7

Met Ser Lys Glu Lys Phe Glu Arg Thr Lys Pro His Val Asn Val Gly
1               5                   10                  15

Thr Ile Gly His Val Asp His Gly Lys Thr Thr Leu Thr Ala Ala Ile
            20                  25                  30

Thr Thr Val Leu Ala Lys Thr Tyr Gly Gly Ala Ala Arg Ala Phe Asp
        35                  40                  45

Gln Ile Asp Asn Ala Pro Glu Glu Lys Ala Arg Gly Ile Thr Ile Asn
    50                  55                  60
```

```
Thr Ser Arg Val Glu Tyr Asp Thr Pro Thr Arg His Tyr Ala His Val
 65                  70                  75                  80

Asp Cys Pro Gly His Ala Asp Tyr Val Lys Asn Met Ile Thr Gly Ala
                 85                  90                  95

Ala Gln Met Asp Gly Ala Ile Leu Val Ala Ala Thr Asp Gly Pro
            100                 105                 110

Met Pro Gln Thr Arg Glu His Ile Leu Leu Gly Arg Gln Val Gly Val
            115                 120                 125

Pro Tyr Ile Ile Val Phe Leu Asn Lys Cys Asp Met Val Asp Asp Glu
            130                 135                 140

Glu Leu Leu Glu Leu Val Glu Met Glu Val Arg Glu Leu Leu Ser Gln
145                 150                 155                 160

Tyr Asp Phe Pro Gly Asp Asp Thr Pro Ile Val Arg Gly Ser Ala Leu
                165                 170                 175

Lys Ala Leu Glu Gly Asp Ala Glu Trp Glu Ala Lys Ile Leu Glu Leu
            180                 185                 190

Ala Gly Phe Leu Asp Ser Tyr Ile Pro Glu Pro Glu Arg Ala Ile Asp
            195                 200                 205

Lys Pro Phe Leu Leu Pro Ile Ala Gly Val Tyr Ser Ile Ser Gly Arg
210                 215                 220

Gly Thr Val Val Ser Gly Arg Val Glu Arg Gly Ile Ile Lys Val Gly
225                 230                 235                 240

Glu Glu Val Glu Ile Val Gly Ile Lys Glu Thr Gln Lys Ser Thr Cys
                245                 250                 255

Thr Gly Val Glu Met Phe Arg Lys Leu Leu Asp Glu Gly Arg Ala Gly
            260                 265                 270

Glu Trp Val Gly Val Leu Leu Arg Gly Ile Lys Arg Glu Glu Ile Glu
            275                 280                 285

Arg Gly Gln Val Leu Ala Lys Pro Gly Thr Ile Lys Pro His Thr Lys
            290                 295                 300

Phe Glu Ser Glu Val Tyr Ile Leu Ser Lys Asp Glu Gly Gly Arg His
305                 310                 315                 320

Thr Pro Phe Phe Lys Gly Tyr Arg Pro Gln Phe Tyr Phe Arg Thr Thr
                325                 330                 335

Asp Val Thr Gly Thr Ile Glu Leu Pro Glu Gly Val Glu Met Val Met
            340                 345                 350

Pro Gly Asp Asn Ile Lys Met Val Val Thr Leu Ile His Pro Ile Ala
            355                 360                 365

Met Asp Asp Gly Leu Arg Phe Ala Ile Arg Glu Gly Gly Arg Thr Val
            370                 375                 380

Gly Ala Gly Val Val Ala Lys Val Leu Ser
385                 390

<210> SEQ ID NO 8
<211> LENGTH: 394
<212> TYPE: PRT
<213> ORGANISM: Artificial Sequence
<220> FEATURE:
<223> OTHER INFORMATION: synthesized sequence (EF-Sep variant 4)

<400> SEQUENCE: 8

Met Ser Lys Glu Lys Phe Glu Arg Thr Lys Pro His Val Asn Val Gly
 1               5                  10                  15

Thr Ile Gly His Val Asp His Gly Lys Thr Thr Leu Thr Ala Ala Ile
             20                  25                  30
```

Thr Thr Val Leu Ala Lys Thr Tyr Gly Gly Ala Ala Arg Ala Phe Asp
            35                  40                  45

Gln Ile Asp Asn Ala Pro Glu Lys Ala Arg Gly Ile Thr Ile Asn
    50                  55                  60

Thr Ser Arg Val Glu Tyr Asp Thr Pro Thr Arg His Tyr Ala His Val
65                  70                  75                  80

Asp Cys Pro Gly His Ala Asp Tyr Val Lys Asn Met Ile Thr Gly Ala
                85                  90                  95

Ala Gln Met Asp Gly Ala Ile Leu Val Val Ala Ala Thr Asp Gly Pro
            100                 105                 110

Met Pro Gln Thr Arg Glu His Ile Leu Leu Gly Arg Gln Val Gly Val
            115                 120                 125

Pro Tyr Ile Ile Val Phe Leu Asn Lys Cys Asp Met Val Asp Asp Glu
    130                 135                 140

Glu Leu Leu Glu Leu Val Glu Met Glu Val Arg Glu Leu Leu Ser Gln
145                 150                 155                 160

Tyr Asp Phe Pro Gly Asp Asp Thr Pro Ile Val Arg Gly Ser Ala Leu
                165                 170                 175

Lys Ala Leu Glu Gly Asp Ala Glu Trp Glu Ala Lys Ile Leu Glu Leu
            180                 185                 190

Ala Gly Phe Leu Asp Ser Tyr Ile Pro Glu Pro Glu Arg Ala Ile Asp
    195                 200                 205

Lys Pro Phe Leu Leu Pro Ile Asn Gly Val Tyr Ser Ile Ser Gly Arg
    210                 215                 220

Gly Thr Val Val Ala Gly Arg Val Glu Arg Gly Ile Ile Lys Val Gly
225                 230                 235                 240

Glu Glu Val Glu Ile Val Gly Ile Lys Glu Thr Gln Lys Ser Thr Cys
                245                 250                 255

Thr Gly Val Glu Met Phe Arg Lys Leu Leu Asp Glu Gly Arg Ala Gly
            260                 265                 270

Glu Trp Val Gly Val Leu Leu Arg Gly Ile Lys Arg Glu Glu Ile Glu
    275                 280                 285

Arg Gly Gln Val Leu Ala Lys Pro Gly Thr Ile Lys Pro His Thr Lys
290                 295                 300

Phe Glu Ser Glu Val Tyr Ile Leu Ser Lys Asp Glu Gly Gly Arg His
305                 310                 315                 320

Thr Pro Phe Phe Lys Gly Tyr Arg Pro Gln Phe Tyr Phe Arg Thr Thr
                325                 330                 335

Asp Val Thr Gly Thr Ile Glu Leu Pro Glu Gly Val Glu Met Val Met
            340                 345                 350

Pro Gly Asp Asn Ile Lys Met Val Val Thr Leu Ile His Pro Ile Ala
            355                 360                 365

Met Asp Asp Gly Leu Arg Phe Ala Ile Arg Glu Gly Gly Arg Thr Val
    370                 375                 380

Gly Ala Gly Val Val Ala Lys Val Leu Ser
385                 390

<210> SEQ ID NO 9
<211> LENGTH: 394
<212> TYPE: PRT
<213> ORGANISM: Artificial Sequence
<220> FEATURE:
<223> OTHER INFORMATION: synthesized sequence (EF-Sep variant 5)

<400> SEQUENCE: 9

```
Met Ser Lys Glu Lys Phe Glu Arg Thr Lys Pro His Val Asn Val Gly
1               5                   10                  15

Thr Ile Gly His Val Asp His Gly Lys Thr Thr Leu Thr Ala Ala Ile
            20                  25                  30

Thr Thr Val Leu Ala Lys Thr Tyr Gly Gly Ala Ala Arg Ala Phe Asp
        35                  40                  45

Gln Ile Asp Asn Ala Pro Glu Glu Lys Ala Arg Gly Ile Thr Ile Asn
50                  55                  60

Thr Ser Arg Val Glu Tyr Asp Thr Pro Thr Arg His Tyr Ala His Val
65                  70                  75                  80

Asp Cys Pro Gly His Ala Asp Tyr Val Lys Asn Met Ile Thr Gly Ala
                85                  90                  95

Ala Gln Met Asp Gly Ala Ile Leu Val Val Ala Ala Thr Asp Gly Pro
            100                 105                 110

Met Pro Gln Thr Arg Glu His Ile Leu Leu Gly Arg Gln Val Gly Val
        115                 120                 125

Pro Tyr Ile Ile Val Phe Leu Asn Lys Cys Asp Met Val Asp Asp Glu
    130                 135                 140

Glu Leu Leu Glu Leu Val Glu Met Glu Val Arg Glu Leu Leu Ser Gln
145                 150                 155                 160

Tyr Asp Phe Pro Gly Asp Thr Pro Ile Val Arg Gly Ser Ala Leu
                165                 170                 175

Lys Ala Leu Glu Gly Asp Ala Glu Trp Glu Ala Lys Ile Leu Glu Leu
            180                 185                 190

Ala Gly Phe Leu Asp Ser Tyr Ile Pro Glu Pro Glu Arg Ala Ile Asp
        195                 200                 205

Lys Pro Phe Leu Leu Pro Ile Asn Gly Val Tyr Ser Ile Ser Gly Arg
    210                 215                 220

Gly Thr Val Val Ser Gly Arg Val Glu Arg Gly Ile Ile Lys Val Gly
225                 230                 235                 240

Glu Glu Val Glu Ile Val Gly Ile Lys Glu Thr Gln Lys Ser Thr Cys
                245                 250                 255

Thr Gly Val Glu Met Phe Arg Lys Leu Leu Asp Glu Gly Arg Ala Gly
            260                 265                 270

Glu Ala Val Gly Val Leu Leu Arg Gly Ile Lys Arg Glu Glu Ile Glu
        275                 280                 285

Arg Gly Gln Val Leu Ala Lys Pro Gly Thr Ile Lys Pro His Thr Lys
    290                 295                 300

Phe Glu Ser Glu Val Tyr Ile Leu Ser Lys Asp Glu Gly Gly Arg His
305                 310                 315                 320

Thr Pro Phe Phe Lys Gly Tyr Arg Pro Gln Phe Tyr Phe Arg Thr Thr
                325                 330                 335

Asp Val Thr Gly Thr Ile Glu Leu Pro Glu Gly Val Glu Met Val Met
            340                 345                 350

Pro Gly Asp Asn Ile Lys Met Val Val Thr Leu Ile His Pro Ile Ala
        355                 360                 365

Met Asp Asp Gly Leu Arg Phe Ala Ile Arg Glu Gly Gly Arg Thr Val
    370                 375                 380

Gly Ala Gly Val Val Ala Lys Val Leu Ser
385                 390

<210> SEQ ID NO 10
<211> LENGTH: 394
<212> TYPE: PRT
```

<213> ORGANISM: Artificial Sequence
<220> FEATURE:
<223> OTHER INFORMATION: synthesized sequence (EF-Sep variant 22)

<400> SEQUENCE: 10

| | | | | | | | | | | | | | | |
|---|---|---|---|---|---|---|---|---|---|---|---|---|---|---|
| Met | Ser | Lys | Glu | Lys | Phe | Glu | Arg | Thr | Lys | Pro | His | Val | Asn | Val | Gly |
| 1 | | | | 5 | | | | | 10 | | | | | 15 | |
| Thr | Ile | Gly | His | Val | Asp | His | Gly | Lys | Thr | Thr | Leu | Thr | Ala | Ala | Ile |
| | | | 20 | | | | | 25 | | | | | 30 | | |
| Thr | Thr | Val | Leu | Ala | Lys | Thr | Tyr | Gly | Ala | Ala | Arg | Ala | Phe | Asp | |
| | | 35 | | | | | 40 | | | | | 45 | | | |
| Gln | Ile | Asp | Asn | Ala | Pro | Glu | Glu | Lys | Ala | Arg | Gly | Ile | Thr | Ile | Asn |
| 50 | | | | | 55 | | | | | 60 | | | | | |
| Thr | Ser | Arg | Val | Glu | Tyr | Asp | Thr | Pro | Thr | Arg | His | Tyr | Ala | His | Val |
| 65 | | | | 70 | | | | | 75 | | | | | 80 | |
| Asp | Cys | Pro | Gly | His | Ala | Asp | Tyr | Val | Lys | Asn | Met | Ile | Thr | Gly | Ala |
| | | | | 85 | | | | 90 | | | | | 95 | | |
| Ala | Gln | Met | Asp | Gly | Ala | Ile | Leu | Val | Val | Ala | Ala | Thr | Asp | Gly | Pro |
| | | | 100 | | | | | 105 | | | | | 110 | | |
| Met | Pro | Gln | Thr | Arg | Glu | His | Ile | Leu | Leu | Gly | Arg | Gln | Val | Gly | Val |
| | | | 115 | | | | | 120 | | | | | 125 | | |
| Pro | Tyr | Ile | Ile | Val | Phe | Leu | Asn | Lys | Cys | Asp | Met | Val | Asp | Asp | Glu |
| | 130 | | | | | 135 | | | | | 140 | | | | |
| Glu | Leu | Leu | Glu | Leu | Val | Glu | Met | Glu | Val | Arg | Glu | Leu | Leu | Ser | Gln |
| 145 | | | | | 150 | | | | | 155 | | | | | 160 |
| Tyr | Asp | Phe | Pro | Gly | Asp | Asp | Thr | Pro | Ile | Val | Arg | Gly | Ser | Ala | Leu |
| | | | | 165 | | | | | 170 | | | | | 175 | |
| Lys | Ala | Leu | Glu | Gly | Asp | Ala | Glu | Trp | Glu | Ala | Lys | Ile | Leu | Glu | Leu |
| | | | 180 | | | | | 185 | | | | | 190 | | |
| Ala | Gly | Phe | Leu | Asp | Ser | Tyr | Ile | Pro | Glu | Pro | Glu | Arg | Ala | Ile | Asp |
| | | 195 | | | | | 200 | | | | | 205 | | | |
| Lys | Pro | Phe | Leu | Leu | Pro | Ile | Tyr | Gly | Val | Tyr | Ser | Ile | Ser | Gly | Arg |
| | 210 | | | | | 215 | | | | | 220 | | | | |
| Gly | Thr | Val | Val | Ser | Gly | Arg | Val | Glu | Arg | Gly | Ile | Ile | Lys | Val | Gly |
| 225 | | | | | 230 | | | | | 235 | | | | | 240 |
| Glu | Glu | Val | Glu | Ile | Val | Gly | Ile | Lys | Glu | Thr | Gln | Lys | Ser | Thr | Cys |
| | | | | 245 | | | | | 250 | | | | | 255 | |
| Thr | Gly | Val | Glu | Met | Phe | Arg | Lys | Leu | Leu | Asp | Glu | Gly | Arg | Ala | Gly |
| | | | 260 | | | | | 265 | | | | | 270 | | |
| Glu | Trp | Val | Gly | Val | Leu | Leu | Arg | Gly | Ile | Lys | Arg | Glu | Glu | Ile | Glu |
| | | 275 | | | | | 280 | | | | | 285 | | | |
| Arg | Gly | Gln | Val | Leu | Ala | Lys | Pro | Gly | Thr | Ile | Lys | Pro | His | Thr | Lys |
| | 290 | | | | | 295 | | | | | 300 | | | | |
| Phe | Glu | Ser | Glu | Val | Tyr | Ile | Leu | Ser | Lys | Asp | Glu | Gly | Gly | Arg | His |
| 305 | | | | | 310 | | | | | 315 | | | | | 320 |
| Thr | Pro | Phe | Phe | Lys | Gly | Tyr | Arg | Pro | Gln | Phe | Tyr | Phe | Arg | Thr | Thr |
| | | | | 325 | | | | | 330 | | | | | 335 | |
| Asp | Val | Thr | Gly | Thr | Ile | Glu | Leu | Pro | Glu | Gly | Val | Glu | Met | Val | Met |
| | | | 340 | | | | | 345 | | | | | 350 | | |
| Pro | Gly | Asp | Asn | Ile | Lys | Met | Val | Thr | Leu | Ile | His | Pro | Ile | Ala | |
| | | | 355 | | | | | 360 | | | | | 365 | | |
| Met | Asp | Asp | Gly | Leu | Arg | Phe | Ala | Ile | Arg | Glu | Gly | Gly | Arg | Thr | Val |
| | 370 | | | | | 375 | | | | | 380 | | | | |
| Gly | Ala | Gly | Val | Val | Ala | Lys | Val | Leu | Ser | | | | | | |

385            390

<210> SEQ ID NO 11
<211> LENGTH: 394
<212> TYPE: PRT
<213> ORGANISM: Artificial Sequence
<220> FEATURE:
<223> OTHER INFORMATION: synthesized sequence (EF-Sep variant 23)

<400> SEQUENCE: 11

Met Ser Lys Glu Lys Phe Glu Arg Thr Lys Pro His Val Asn Val Gly
1               5                   10                  15

Thr Ile Gly His Val Asp His Gly Lys Thr Thr Leu Thr Ala Ala Ile
            20                  25                  30

Thr Thr Val Leu Ala Lys Thr Tyr Gly Gly Ala Ala Arg Ala Phe Asp
        35                  40                  45

Gln Ile Asp Asn Ala Pro Glu Glu Lys Ala Arg Gly Ile Thr Ile Asn
    50                  55                  60

Thr Ser Arg Val Glu Tyr Asp Thr Pro Thr Arg His Tyr Ala His Val
65                  70                  75                  80

Asp Cys Pro Gly His Ala Asp Tyr Val Lys Asn Met Ile Thr Gly Ala
                85                  90                  95

Ala Gln Met Asp Gly Ala Ile Leu Val Val Ala Ala Thr Asp Gly Pro
            100                 105                 110

Met Pro Gln Thr Arg Glu His Ile Leu Leu Gly Arg Gln Val Gly Val
        115                 120                 125

Pro Tyr Ile Ile Val Phe Leu Asn Lys Cys Asp Met Val Asp Asp Glu
    130                 135                 140

Glu Leu Leu Glu Leu Val Glu Met Glu Val Arg Glu Leu Leu Ser Gln
145                 150                 155                 160

Tyr Asp Phe Pro Gly Asp Asp Thr Pro Ile Val Arg Gly Ser Ala Leu
                165                 170                 175

Lys Ala Leu Glu Gly Asp Ala Glu Trp Glu Ala Lys Ile Leu Glu Leu
            180                 185                 190

Ala Gly Phe Leu Asp Ser Tyr Ile Pro Glu Pro Glu Arg Ala Ile Asp
        195                 200                 205

Lys Pro Phe Leu Leu Pro Ile Cys Gly Val Tyr Ser Ile Ser Gly Arg
    210                 215                 220

Gly Thr Val Val Ser Gly Arg Val Glu Arg Gly Ile Ile Lys Val Gly
225                 230                 235                 240

Glu Glu Val Glu Ile Val Gly Ile Lys Glu Thr Gln Lys Ser Thr Cys
                245                 250                 255

Thr Gly Val Glu Met Phe Arg Lys Leu Leu Asp Glu Gly Arg Ala Gly
            260                 265                 270

Glu Trp Val Gly Val Leu Leu Arg Gly Ile Lys Arg Glu Glu Ile Glu
        275                 280                 285

Arg Gly Gln Val Leu Ala Lys Pro Gly Thr Ile Lys Pro His Thr Lys
    290                 295                 300

Phe Glu Ser Glu Val Tyr Ile Leu Ser Lys Asp Glu Gly Gly Arg His
305                 310                 315                 320

Thr Pro Phe Phe Lys Gly Tyr Arg Pro Gln Phe Tyr Phe Arg Thr Thr
                325                 330                 335

Asp Val Thr Gly Thr Ile Glu Leu Pro Glu Gly Val Glu Met Val Met
            340                 345                 350

Pro Gly Asp Asn Ile Lys Met Val Val Thr Leu Ile His Pro Ile Ala

```
            355                 360                 365
Met Asp Asp Gly Leu Arg Phe Ala Ile Arg Glu Gly Arg Thr Val
    370                 375                 380

Gly Ala Gly Val Val Ala Lys Val Leu Ser
385                 390

<210> SEQ ID NO 12
<211> LENGTH: 394
<212> TYPE: PRT
<213> ORGANISM: Artificial Sequence
<220> FEATURE:
<223> OTHER INFORMATION: synthesized sequence (EF-Sep variant 24)

<400> SEQUENCE: 12

Met Ser Lys Glu Lys Phe Glu Arg Thr Lys Pro His Val Asn Val Gly
1               5                   10                  15

Thr Ile Gly His Val Asp His Gly Lys Thr Thr Leu Thr Ala Ala Ile
            20                  25                  30

Thr Thr Val Leu Ala Lys Thr Tyr Gly Gly Ala Ala Arg Ala Phe Asp
        35                  40                  45

Gln Ile Asp Asn Ala Pro Glu Glu Lys Ala Arg Gly Ile Thr Ile Asn
    50                  55                  60

Thr Ser Arg Val Glu Tyr Asp Thr Pro Thr Arg His Tyr Ala His Val
65                  70                  75                  80

Asp Cys Pro Gly His Ala Asp Tyr Val Lys Asn Met Ile Thr Gly Ala
                85                  90                  95

Ala Gln Met Asp Gly Ala Ile Leu Val Val Ala Ala Thr Asp Gly Pro
            100                 105                 110

Met Pro Gln Thr Arg Glu His Ile Leu Leu Gly Arg Gln Val Gly Val
        115                 120                 125

Pro Tyr Ile Ile Val Phe Leu Asn Lys Cys Asp Met Val Asp Asp Glu
    130                 135                 140

Glu Leu Leu Glu Leu Val Glu Met Glu Val Arg Glu Leu Leu Ser Gln
145                 150                 155                 160

Tyr Asp Phe Pro Gly Asp Asp Thr Pro Ile Val Arg Gly Ser Ala Leu
                165                 170                 175

Lys Ala Leu Glu Gly Asp Ala Glu Trp Glu Ala Lys Ile Leu Glu Leu
            180                 185                 190

Ala Gly Phe Leu Asp Ser Tyr Ile Pro Glu Pro Glu Arg Ala Ile Asp
        195                 200                 205

Lys Pro Phe Leu Leu Pro Ile Arg Gly Val Tyr Ser Ile Ser Gly Arg
    210                 215                 220

Gly Thr Val Val Ser Gly Arg Val Glu Arg Gly Ile Ile Lys Val Gly
225                 230                 235                 240

Glu Glu Val Glu Ile Val Gly Ile Lys Glu Thr Gln Lys Ser Thr Cys
                245                 250                 255

Thr Gly Val Glu Met Phe Arg Lys Leu Leu Asp Glu Gly Arg Ala Gly
            260                 265                 270

Glu Trp Val Gly Val Leu Leu Arg Gly Ile Lys Arg Glu Glu Ile Glu
        275                 280                 285

Arg Gly Gln Val Leu Ala Lys Pro Gly Thr Ile Lys Pro His Thr Lys
    290                 295                 300

Phe Glu Ser Glu Val Tyr Ile Leu Ser Lys Asp Glu Gly Gly Arg His
305                 310                 315                 320

Thr Pro Phe Phe Lys Gly Tyr Arg Pro Gln Phe Tyr Phe Arg Thr Thr
```

```
            325                 330                 335
Asp Val Thr Gly Thr Ile Glu Leu Pro Glu Gly Val Glu Met Val Met
            340                 345                 350

Pro Gly Asp Asn Ile Lys Met Val Val Thr Leu Ile His Pro Ile Ala
            355                 360                 365

Met Asp Asp Gly Leu Arg Phe Ala Ile Arg Glu Gly Arg Thr Val
370                 375                 380

Gly Ala Gly Val Val Ala Lys Val Leu Ser
385                 390

<210> SEQ ID NO 13
<211> LENGTH: 394
<212> TYPE: PRT
<213> ORGANISM: Artificial Sequence
<220> FEATURE:
<223> OTHER INFORMATION: synthesized sequence (EF-Sep variant 25)

<400> SEQUENCE: 13

Met Ser Lys Glu Lys Phe Glu Arg Thr Lys Pro His Val Asn Val Gly
1               5                   10                  15

Thr Ile Gly His Val Asp His Gly Lys Thr Thr Leu Thr Ala Ala Ile
            20                  25                  30

Thr Thr Val Leu Ala Lys Thr Tyr Gly Gly Ala Ala Arg Ala Phe Asp
        35                  40                  45

Gln Ile Asp Asn Ala Pro Glu Glu Lys Ala Arg Gly Ile Thr Ile Asn
    50                  55                  60

Thr Ser Arg Val Glu Tyr Asp Thr Pro Thr Arg His Tyr Ala His Val
65                  70                  75                  80

Asp Cys Pro Gly His Ala Asp Tyr Val Lys Asn Met Ile Thr Gly Ala
                85                  90                  95

Ala Gln Met Asp Gly Ala Ile Leu Val Val Ala Ala Thr Asp Gly Pro
            100                 105                 110

Met Pro Gln Thr Arg Glu His Ile Leu Leu Gly Arg Gln Val Gly Val
        115                 120                 125

Pro Tyr Ile Ile Val Phe Leu Asn Lys Cys Asp Met Val Asp Asp Glu
    130                 135                 140

Glu Leu Leu Glu Leu Val Glu Met Glu Val Arg Glu Leu Leu Ser Gln
145                 150                 155                 160

Tyr Asp Phe Pro Gly Asp Asp Thr Pro Ile Val Arg Gly Ser Ala Leu
                165                 170                 175

Lys Ala Leu Glu Gly Asp Ala Glu Trp Glu Ala Lys Ile Leu Glu Leu
            180                 185                 190

Ala Gly Phe Leu Asp Ser Tyr Ile Pro Glu Pro Glu Arg Ala Ile Asp
        195                 200                 205

Lys Pro Phe Leu Leu Pro Ile Thr Gly Val Tyr Ser Ile Ser Gly Arg
    210                 215                 220

Gly Thr Val Val Ser Gly Arg Val Glu Arg Gly Ile Ile Lys Val Gly
225                 230                 235                 240

Glu Glu Val Glu Ile Val Gly Ile Lys Glu Thr Gln Lys Ser Thr Cys
                245                 250                 255

Thr Gly Val Glu Met Phe Arg Lys Leu Leu Asp Glu Gly Arg Ala Gly
            260                 265                 270

Glu Trp Val Gly Val Leu Leu Arg Gly Ile Lys Arg Glu Glu Ile Glu
        275                 280                 285

Arg Gly Gln Val Leu Ala Lys Pro Gly Thr Ile Lys Pro His Thr Lys
```

```
                290                 295                 300
Phe Glu Ser Glu Val Tyr Ile Leu Ser Lys Asp Glu Gly Arg His
305                 310                 315                 320

Thr Pro Phe Phe Lys Gly Tyr Arg Pro Gln Phe Tyr Phe Arg Thr Thr
                325                 330                 335

Asp Val Thr Gly Thr Ile Glu Leu Pro Glu Gly Val Glu Met Val Met
                340                 345                 350

Pro Gly Asp Asn Ile Lys Met Val Val Thr Leu Ile His Pro Ile Ala
                355                 360                 365

Met Asp Asp Gly Leu Arg Phe Ala Ile Arg Glu Gly Gly Arg Thr Val
                370                 375                 380

Gly Ala Gly Val Val Ala Lys Val Leu Ser
385                 390

<210> SEQ ID NO 14
<211> LENGTH: 394
<212> TYPE: PRT
<213> ORGANISM: Artificial Sequence
<220> FEATURE:
<223> OTHER INFORMATION: synthesized sequence (EF-Sep variant 26)

<400> SEQUENCE: 14

Met Ser Lys Glu Lys Phe Glu Arg Thr Lys Pro His Val Asn Val Gly
1               5                   10                  15

Thr Ile Gly His Val Asp His Gly Lys Thr Thr Leu Thr Ala Ala Ile
                20                  25                  30

Thr Thr Val Leu Ala Lys Thr Tyr Gly Gly Ala Ala Arg Ala Phe Asp
                35                  40                  45

Gln Ile Asp Asn Ala Pro Glu Glu Lys Ala Arg Gly Ile Thr Ile Asn
            50                  55                  60

Thr Ser Arg Val Glu Tyr Asp Thr Pro Thr Arg His Tyr Ala His Val
65                  70                  75                  80

Asp Cys Pro Gly His Ala Asp Tyr Val Lys Asn Met Ile Thr Gly Ala
                85                  90                  95

Ala Gln Met Asp Gly Ala Ile Leu Val Val Ala Thr Asp Gly Pro
                100                 105                 110

Met Pro Gln Thr Arg Glu His Ile Leu Leu Gly Arg Gln Val Gly Val
                115                 120                 125

Pro Tyr Ile Ile Val Phe Leu Asn Lys Cys Asp Met Val Asp Asp Glu
                130                 135                 140

Glu Leu Leu Glu Leu Val Glu Met Glu Val Arg Glu Leu Leu Ser Gln
145                 150                 155                 160

Tyr Asp Phe Pro Gly Asp Asp Thr Pro Ile Val Arg Gly Ser Ala Leu
                165                 170                 175

Lys Ala Leu Glu Gly Asp Ala Glu Trp Glu Ala Lys Ile Leu Glu Leu
                180                 185                 190

Ala Gly Phe Leu Asp Ser Tyr Ile Pro Glu Pro Glu Arg Ala Ile Asp
                195                 200                 205

Lys Pro Phe Leu Leu Pro Ile Leu Gly Val Tyr Ser Ile Ser Gly Arg
                210                 215                 220

Gly Thr Val Val Ser Gly Arg Val Glu Arg Gly Ile Ile Lys Val Gly
225                 230                 235                 240

Glu Glu Val Glu Ile Val Gly Ile Lys Glu Thr Gln Lys Ser Thr Cys
                245                 250                 255

Thr Gly Val Glu Met Phe Arg Lys Leu Leu Asp Glu Gly Arg Ala Gly
```

```
              260                 265                 270
Glu Trp Val Gly Val Leu Leu Arg Gly Ile Lys Arg Glu Ile Glu
            275                 280                 285
Arg Gly Gln Val Leu Ala Lys Pro Gly Thr Ile Lys Pro His Thr Lys
        290                 295                 300
Phe Glu Ser Glu Val Tyr Ile Leu Ser Lys Asp Gly Gly Arg His
305                 310                 315                 320
Thr Pro Phe Phe Lys Gly Tyr Arg Pro Gln Phe Tyr Phe Arg Thr Thr
                325                 330                 335
Asp Val Thr Gly Thr Ile Glu Leu Pro Glu Gly Val Glu Met Val Met
            340                 345                 350
Pro Gly Asp Asn Ile Lys Met Val Val Thr Leu Ile His Pro Ile Ala
            355                 360                 365
Met Asp Asp Gly Leu Arg Phe Ala Ile Arg Glu Gly Gly Arg Thr Val
            370                 375                 380
Gly Ala Gly Val Val Ala Lys Val Leu Ser
385                 390

<210> SEQ ID NO 15
<211> LENGTH: 1185
<212> TYPE: DNA
<213> ORGANISM: Artificial Sequence
<220> FEATURE:
<223> OTHER INFORMATION: synthesized sequence (EF-Sep variant 21)

<400> SEQUENCE: 15
atgtctaaag aaaagtttga acgtacaaaa ccgcacgtta acgtcggtac tatcggccac     60
gttgaccatg gtaaaacaac gctgaccgct gcaatcacta ccgtactggc taaaacctac    120
ggcggtgctg ctcgcgcatt cgaccagatc gataacgcgc ggaagaaaa agctcgtggt    180 atcaccatca acacttctcg ggttgaatac gacaccccga cccgtcacta cgcacacgta    240
gactgcccgg gcacgccga ctatgttaaa aacatgatca ccggtgctgc gcagatggac    300
ggcgcgatcc tggtagttgc tgcgactgac ggcccgatgc cgcagactcg tgagcacatc    360
ctgctgggtc gtcaggtagg cgttccgtac atcatcgtgt tcctgaacaa atgcgacatg    420
gttgatgacg aagagctgct ggaactggtt gaaatggaag ttcgtgaact tctgtctcag    480
tacgacttcc cgggcgacga cactccgatc gttcgtggtt ctgctctgaa agcgctggaa    540
ggcgacgcag agtgggaagc gaaaatcctg gaactggctg gcttcctgga ttcttacatt    600
ccggaaccag agcgtgcgat tgacaagccg ttcctgctgc cgatcgtggg ggtatactcc    660
atctccggtc gtggtaccgt tgtttcgggt cgtgtagaac gcggtatcat caaagttggt    720
gaagaagttg aaatcgttgg tatcaaagag actcagaagt ctacctgtac tggcgttgaa    780
atgttccgca aactgctgga cgaaggccgt gctggtgagt gggtaggtgt tctgctgcgt    840
ggtatcaaac gtgaagaaat cgaacgtggt caggtactgg ctaagccggg caccatcaag    900
ccgcacacca gttcgaatc tgaagtgtac attctgtcca agatgaaagg cggccgtcat    960
actccgttct tcaaaggcta ccgtccgcag ttctacttcc gtactactga cgtgactggt   1020
accatcgaac tgccggaagg cgtagagatg gtaatgccgg cgacaacat caaaatggtt   1080 gttaccctga tccacccgat cgcgatggac gacggtctgc gtttcgcaat ccgtgaaggc   1140
ggccgtaccg ttggcgcggg cgttgtagca aaagttctga gctaa                  1185

<210> SEQ ID NO 16
<211> LENGTH: 75
```

```
<212> TYPE: RNA
<213> ORGANISM: Methanocaldococcus jannaschii

<400> SEQUENCE: 16 gccggggguag ucuaggggvu aggcagcgga cucuagaucc gccuuacgug gguucaaauc    60
ccacccccgg cucca                                                     75

<210> SEQ ID NO 17
<211> LENGTH: 537
<212> TYPE: PRT
<213> ORGANISM: Methanococcus maripaludis

<400> SEQUENCE: 17
```

| Met | Phe | Lys | Arg | Glu | Glu | Ile | Ile | Glu | Met | Ala | Asn | Lys | Asp | Phe | Glu |
|---|---|---|---|---|---|---|---|---|---|---|---|---|---|---|---|
| 1 | | | | 5 | | | | | 10 | | | | | 15 | |

| Lys | Ala | Trp | Ile | Glu | Thr | Lys | Asp | Leu | Ile | Lys | Ala | Lys | Lys | Ile | Asn |
|---|---|---|---|---|---|---|---|---|---|---|---|---|---|---|---|
| | | | 20 | | | | | 25 | | | | | 30 | | |

| Glu | Ser | Tyr | Pro | Arg | Ile | Lys | Pro | Val | Phe | Gly | Lys | Thr | His | Pro | Val |
|---|---|---|---|---|---|---|---|---|---|---|---|---|---|---|---|
| | | 35 | | | | | 40 | | | | | 45 | | | |

| Asn | Asp | Thr | Ile | Glu | Asn | Leu | Arg | Gln | Ala | Tyr | Leu | Arg | Met | Gly | Phe |
|---|---|---|---|---|---|---|---|---|---|---|---|---|---|---|---|
| | 50 | | | | | 55 | | | | | 60 | | | | |

| Glu | Glu | Tyr | Ile | Asn | Pro | Val | Ile | Val | Asp | Glu | Arg | Asp | Ile | Tyr | Lys |
|---|---|---|---|---|---|---|---|---|---|---|---|---|---|---|---|
| 65 | | | | | 70 | | | | | 75 | | | | | 80 |

| Gln | Phe | Gly | Pro | Glu | Ala | Met | Ala | Val | Leu | Asp | Arg | Cys | Phe | Tyr | Leu |
|---|---|---|---|---|---|---|---|---|---|---|---|---|---|---|---|
| | | | | 85 | | | | | 90 | | | | | 95 | |

| Ala | Gly | Leu | Pro | Arg | Pro | Asp | Val | Gly | Leu | Ser | Asp | Glu | Lys | Ile | Ser |
|---|---|---|---|---|---|---|---|---|---|---|---|---|---|---|---|
| | | | 100 | | | | | 105 | | | | | 110 | | |

| Gln | Ile | Glu | Lys | Leu | Gly | Ile | Lys | Val | Ser | Glu | His | Lys | Glu | Ser | Leu |
|---|---|---|---|---|---|---|---|---|---|---|---|---|---|---|---|
| | | 115 | | | | | 120 | | | | | 125 | | | |

| Gln | Lys | Ile | Leu | His | Gly | Tyr | Lys | Lys | Gly | Thr | Leu | Asp | Gly | Asp | Asp |
|---|---|---|---|---|---|---|---|---|---|---|---|---|---|---|---|
| | 130 | | | | | 135 | | | | | 140 | | | | |

| Leu | Val | Leu | Glu | Ile | Ser | Asn | Ala | Leu | Glu | Ile | Ser | Ser | Glu | Met | Gly |
|---|---|---|---|---|---|---|---|---|---|---|---|---|---|---|---|
| 145 | | | | | 150 | | | | | 155 | | | | | 160 |

| Leu | Lys | Ile | Leu | Glu | Asp | Val | Phe | Pro | Glu | Phe | Lys | Asp | Leu | Thr | Ala |
|---|---|---|---|---|---|---|---|---|---|---|---|---|---|---|---|
| | | | | 165 | | | | | 170 | | | | | 175 | |

| Val | Ser | Ser | Lys | Leu | Thr | Leu | Arg | Ser | His | Met | Thr | Ser | Gly | Trp | Phe |
|---|---|---|---|---|---|---|---|---|---|---|---|---|---|---|---|
| | | | 180 | | | | | 185 | | | | | 190 | | |

| Leu | Thr | Val | Ser | Asp | Leu | Met | Asn | Lys | Lys | Pro | Leu | Pro | Phe | Lys | Leu |
|---|---|---|---|---|---|---|---|---|---|---|---|---|---|---|---|
| | | 195 | | | | | 200 | | | | | 205 | | | |

| Phe | Ser | Ile | Asp | Arg | Cys | Phe | Arg | Arg | Glu | Gln | Lys | Glu | Asp | Lys | Ser |
|---|---|---|---|---|---|---|---|---|---|---|---|---|---|---|---|
| | 210 | | | | | 215 | | | | | 220 | | | | |

| His | Leu | Met | Thr | Tyr | His | Ser | Ala | Ser | Cys | Ala | Ile | Ala | Gly | Glu | Gly |
|---|---|---|---|---|---|---|---|---|---|---|---|---|---|---|---|
| 225 | | | | | 230 | | | | | 235 | | | | | 240 |

| Val | Asp | Ile | Asn | Asp | Gly | Lys | Ala | Ile | Ala | Glu | Gly | Leu | Leu | Ser | Gln |
|---|---|---|---|---|---|---|---|---|---|---|---|---|---|---|---|
| | | | | 245 | | | | | 250 | | | | | 255 | |

| Phe | Gly | Phe | Thr | Asn | Phe | Lys | Phe | Ile | Pro | Asp | Glu | Lys | Lys | Ser | Lys |
|---|---|---|---|---|---|---|---|---|---|---|---|---|---|---|---|
| | | | 260 | | | | | 265 | | | | | 270 | | |

| Tyr | Tyr | Thr | Pro | Glu | Thr | Gln | Thr | Glu | Val | Tyr | Ala | Tyr | His | Pro | Lys |
|---|---|---|---|---|---|---|---|---|---|---|---|---|---|---|---|
| | | 275 | | | | | 280 | | | | | 285 | | | |

| Leu | Lys | Glu | Trp | Leu | Glu | Val | Ala | Thr | Phe | Gly | Val | Tyr | Ser | Pro | Val |
|---|---|---|---|---|---|---|---|---|---|---|---|---|---|---|---|
| | 290 | | | | | 295 | | | | | 300 | | | | |

| Ala | Leu | Ser | Lys | Tyr | Gly | Ile | Asp | Val | Pro | Val | Met | Asn | Leu | Gly | Leu |
|---|---|---|---|---|---|---|---|---|---|---|---|---|---|---|---|
| 305 | | | | | 310 | | | | | 315 | | | | | 320 |

| Gly | Val | Glu | Arg | Leu | Ala | Met | Ile | Ser | Gly | Asn | Phe | Ala | Asp | Val | Arg |
|---|---|---|---|---|---|---|---|---|---|---|---|---|---|---|---|
| | | | | 325 | | | | | 330 | | | | | 335 | |

```
Glu Met Val Tyr Pro Gln Phe Tyr Glu His Lys Leu Asn Asp Arg Asn
                340                 345                 350

Val Ala Ser Met Val Lys Leu Asp Lys Val Pro Val Met Asp Glu Ile
            355                 360                 365

Tyr Asp Leu Thr Lys Glu Leu Ile Glu Ser Cys Val Lys Asn Lys Asp
        370                 375                 380

Leu Lys Ser Pro Cys Glu Leu Ala Ile Glu Lys Thr Phe Ser Phe Gly
385                 390                 395                 400

Lys Thr Lys Lys Asn Val Lys Ile Asn Ile Phe Glu Lys Glu Glu Gly
                405                 410                 415

Lys Asn Leu Leu Gly Pro Ser Ile Leu Asn Glu Ile Tyr Val Tyr Asp
            420                 425                 430

Gly Asn Val Ile Gly Ile Pro Glu Ser Phe Asp Gly Val Lys Glu Glu
        435                 440                 445

Phe Lys Asp Phe Leu Glu Lys Gly Lys Ser Glu Gly Val Ala Thr Gly
    450                 455                 460

Ile Arg Tyr Ile Asp Ala Leu Cys Phe Lys Ile Thr Ser Lys Leu Glu
465                 470                 475                 480

Glu Ala Phe Val Ser Asn Thr Thr Glu Phe Lys Val Lys Val Pro Ile
                485                 490                 495

Val Arg Ser Leu Ser Asp Ile Asn Leu Lys Ile Asp Asp Ile Ala Leu
            500                 505                 510

Lys Gln Ile Met Ser Lys Asn Lys Val Ile Asp Val Arg Gly Pro Val
        515                 520                 525

Phe Leu Asn Val Glu Val Lys Ile Glu
    530                 535

<210> SEQ ID NO 18
<211> LENGTH: 1614
<212> TYPE: DNA
<213> ORGANISM: Methanococcus maripaludis

<400> SEQUENCE: 18
atgtttaaaa gagaagaaat cattgaaatg gccaataagg actttgaaaa agcatggatc      60
gaaactaaag accttataaa agctaaaaag ataaacgaaa gttacccaag aataaaacca     120 gttttttggaa aaacacaccc tgtaaatgac actattgaaa atttaagaca ggcatatctt     180
agaatgggtt ttgaagaata tataaaccca gtaattgtcg atgaaagaga tatttataaa     240
caattcggcc agaagctat ggcagttttg gatagatgct tttatttagc gggacttcca     300
agacctgacg ttggtttgag cgatgaaaaa atttcacaga ttgaaaaact tggaattaaa     360
gtttctgagc acaagaaag tttacaaaaa atacttcacg gatacaaaaa aggaactctt     420
gatggtgacg atttagtttt agaaatttca aatgcacttg aaatttcaag cgagatgggt     480
ttaaaaattt tagaagatgt tttcccagaa tttaaggatt taaccgcagt ttcttcaaaa     540
ttaactttaa gaagccacat gacttcagga tggttcctta ctgtttcaga cctcatgaac     600
aaaaaaccct tgccatttaa actcttttca atcgatagat gttttagaag agaacaaaaa     660
gaagataaaa gccacttaat gacataccac tctgcatcct gtgcaattgc aggtgaaggc     720
gtggatatta tgatggaaa agcaattgca gaaggattat atcccaatt tggctttaca     780 aactttaaat tcattcctga tgaaagaaa agtaaatact acaccctga acacagact     840 gaagtttacg cataccaccc aaaattaaaa gaatggctcg aagttgctac atttggagta     900
tattcgccag ttgcattaag caaatacgga atagatgtac ctgtaatgaa tttgggtctt     960
```

```
ggtgttgaaa gacttgcaat gatttctgga aatttcgcag atgttcgaga aatggtatat    1020
cctcagtttt acgaacacaa acttaatgac cggaatgtcg cttcaatggt aaaactcgat    1080
aaagttccag taatggatga aatttacgat ttaacaaaag aattaattga gtcatgtgtt    1140
aaaaacaaag atttaaaatc cccttgtgaa ttagctattg aaaaaacgtt ttcatttgga    1200 aaaccaaga aaatgtaaa aataaacatt tttgaaaaag aagaaggtaa aaatttactc      1260
ggaccttcaa ttttaaacga aatctacgtt tacgatggaa atgtaattgg aattcctgaa    1320
agctttgacg gagtaaaaga agaatttaaa gacttcttag aaaaaggaaa atcagaaggg    1380
gtagcaacag gcattcgata tatcgatgcg ctttgcttta aaattacttc aaaattagaa    1440
gaagcatttg tgtcaaacac tactgaattc aaagttaaag ttccaattgt cagaagttta    1500
agcgacatta acttaaaaat cgatgatatc gcattaaaac agatcatgag caaaaataaa    1560
gtaatcgacg ttagaggccc agtctttta aatgtcgaag taaaaattga ataa           1614

<210> SEQ ID NO 19
<211> LENGTH: 394
<212> TYPE: PRT
<213> ORGANISM: Escherichia coli

<400> SEQUENCE: 19

Met Ser Lys Glu Lys Phe Glu Arg Thr Lys Pro His Val Asn Val Gly
1               5                   10                  15

Thr Ile Gly His Val Asp His Gly Lys Thr Thr Leu Thr Ala Ala Ile
            20                  25                  30

Thr Thr Val Leu Ala Lys Thr Tyr Gly Gly Ala Ala Arg Ala Phe Asp
        35                  40                  45

Gln Ile Asp Asn Ala Pro Glu Glu Lys Ala Arg Gly Ile Thr Ile Asn
    50                  55                  60

Thr Ser His Val Glu Tyr Asp Thr Pro Thr Arg His Tyr Ala His Val
65                  70                  75                  80

Asp Cys Pro Gly His Ala Asp Tyr Val Lys Asn Met Ile Thr Gly Ala
                85                  90                  95

Ala Gln Met Asp Gly Ala Ile Leu Val Val Ala Ala Thr Asp Gly Pro
            100                 105                 110

Met Pro Gln Thr Arg Glu His Ile Leu Leu Gly Arg Gln Val Gly Val
        115                 120                 125

Pro Tyr Ile Ile Val Phe Leu Asn Lys Cys Asp Met Val Asp Asp Glu
    130                 135                 140

Glu Leu Leu Glu Leu Val Glu Met Glu Val Arg Glu Leu Leu Ser Gln
145                 150                 155                 160

Tyr Asp Phe Pro Gly Asp Asp Thr Pro Ile Val Arg Gly Ser Ala Leu
                165                 170                 175

Lys Ala Leu Glu Gly Asp Ala Glu Trp Glu Ala Lys Ile Leu Glu Leu
            180                 185                 190

Ala Gly Phe Leu Asp Ser Tyr Ile Pro Glu Pro Glu Arg Ala Ile Asp
        195                 200                 205

Lys Pro Phe Leu Leu Pro Ile Glu Asp Val Phe Ser Ile Ser Gly Arg
    210                 215                 220

Gly Thr Val Val Thr Gly Arg Val Glu Arg Gly Ile Ile Lys Val Gly
225                 230                 235                 240

Glu Glu Val Glu Ile Val Gly Ile Lys Glu Thr Gln Lys Ser Thr Cys
                245                 250                 255
```

```
Thr Gly Val Glu Met Phe Arg Lys Leu Leu Asp Glu Gly Arg Ala Gly
            260                 265                 270

Glu Asn Val Gly Val Leu Leu Arg Gly Ile Lys Arg Glu Glu Ile Glu
        275                 280                 285

Arg Gly Gln Val Leu Ala Lys Pro Gly Thr Ile Lys Pro His Thr Lys
    290                 295                 300

Phe Glu Ser Glu Val Tyr Ile Leu Ser Lys Asp Glu Gly Arg His
305                 310                 315                 320

Thr Pro Phe Phe Lys Gly Tyr Arg Pro Gln Phe Tyr Phe Arg Thr Thr
                325                 330                 335

Asp Val Thr Gly Thr Ile Glu Leu Pro Glu Gly Val Glu Met Val Met
            340                 345                 350

Pro Gly Asp Asn Ile Lys Met Val Val Thr Leu Ile His Pro Ile Ala
        355                 360                 365

Met Asp Asp Gly Leu Arg Phe Ala Ile Arg Glu Gly Gly Arg Thr Val
    370                 375                 380

Gly Ala Gly Val Val Ala Lys Val Leu Gly
385                 390

<210> SEQ ID NO 20
<211> LENGTH: 1185
<212> TYPE: DNA
<213> ORGANISM: Escherichia coli

<400> SEQUENCE: 20
gtgtctaaag aaaaatttga acgtacaaaa ccgcacgtta acgttggtac tatcggccac     60
gttgaccacg gtaaaactac tctgaccgct gcaatcacca ccgtactggc taaaacctac     120
ggcggtgctg ctcgtgcatt cgaccagatc gataacgcgc cggaagaaaa agctcgtggt    180
atcaccatca cacttctca cgttgaatac gacaccccga cccgtcacta cgcacacgta    240
gactgcccgg gcacgccga ctatgttaaa aacatgatca ccggtgctgc tcagatggac    300
ggcgcgatcc tggtagttgc tgcgactgac ggcccgatgc cgcagactcg tgagcacatc    360
ctgctgggtc gtcaggtagg cgttccgtac atcatcgtgt tcctgaacaa atgcgacatg    420
gttgatgacg aagagctgct ggaactggtt gaaatggaag ttcgtgaact tctgtctcag    480
tacgacttcc cgggcgacga cactccgatc gttcgtggtt ctgctctgaa agcgctggaa    540
ggcgacgcag agtgggaagc gaaaatcctg gaactggctg cttcctgga ttcttatatt    600 ccggaaccag agcgtgcgat tgacaagccg ttcctgctgc cgatcgaaga cgtattctcc    660
atctccggtc gtggtaccgt tgttaccggt cgtgtagaac gcggtatcat caaagttggt    720
gaagaagttg aaatcgttgg tatcaaagag actcagaagt ctacctgtac tggcgttgaa    780
atgttccgca aactgctgga cgaaggccgt gctggtgaga acgtaggtgt tctgctgcgt    840
ggtatcaaac gtgaagaaat cgaacgtggt caggtactgg ctaagccggg caccatcaag    900
ccgcacacca gttcgaatc tgaagtgtac attctgtcca agatgaagg cggccgtcat    960 actccgttct tcaaaggcta ccgtccgcag ttctacttcc gtactactga cgtgactggt   1020
accatcgaac tgccggaagg cgtagagatg gtaatgccgg cgacaacat caaaatggtt   1080 gttaccctga tccacccgat cgcgatggac gacggtctgc gtttcgcaat ccgtgaaggc   1140
ggccgtaccg ttggcgcggg cgttgttgct aaagttctgg gctaa                   1185

<210> SEQ ID NO 21
<211> LENGTH: 40
<212> TYPE: DNA
```

<210> SEQ ID NO 21
<211> LENGTH: 40
<212> TYPE: DNA
<213> ORGANISM: Artificial Sequence
<220> FEATURE:
<223> OTHER INFORMATION: primer, SP412GCF1

<400> SEQUENCE: 21
gaagagggca agaacctgct cggaccttca attttaaacg　　　　　　　　　　　　　　40

<210> SEQ ID NO 22
<211> LENGTH: 43
<212> TYPE: DNA
<213> ORGANISM: Artificial Sequence
<220> FEATURE:
<223> OTHER INFORMATION: primer, SP412GCF2

<400> SEQUENCE: 22
cgtgaagatc aacatcttcg aaaaagaaga gggcaagaac ctg　　　　　　　　　　　43

<210> SEQ ID NO 23
<211> LENGTH: 41
<212> TYPE: DNA
<213> ORGANISM: Artificial Sequence
<220> FEATURE:
<223> OTHER INFORMATION: primer, SP412GCR

<400> SEQUENCE: 23
gaagatgttg atcttcacgt ttttcttggt ttttccaaat g　　　　　　　　　　　　41

<210> SEQ ID NO 24
<211> LENGTH: 38
<212> TYPE: DNA
<213> ORGANISM: Artificial Sequence
<220> FEATURE:
<223> OTHER INFORMATION: primer, SP130F

<400> SEQUENCE: 24
cgatggaaat gtaattggca ttcctgaaag ctttgacg　　　　　　　　　　　　　　38

<210> SEQ ID NO 25
<211> LENGTH: 18
<212> TYPE: DNA
<213> ORGANISM: Artificial Sequence
<220> FEATURE:
<223> OTHER INFORMATION: primer, SP130R

<400> SEQUENCE: 25
ccaattacat ttccatcg　　　　　　　　　　　　　　　　　　　　　　　　　　18

<210> SEQ ID NO 26
<211> LENGTH: 40
<212> TYPE: DNA
<213> ORGANISM: Artificial Sequence
<220> FEATURE:
<223> OTHER INFORMATION: primer, SP495GCF

<400> SEQUENCE: 26
gagttcaagg tcaaggtgcc aattgtcaga agtttaagcg　　　　　　　　　　　　　40

<210> SEQ ID NO 27
<211> LENGTH: 39
<212> TYPE: DNA
<213> ORGANISM: Artificial Sequence
<220> FEATURE:
<223> OTHER INFORMATION: primer, SP495GCR

<400> SEQUENCE: 27
caccttgacc ttgaactcag tagtgtttga cacaaatgc　　　　　　　　　　　　　　39

<210> SEQ ID NO 28
<211> LENGTH: 41
<212> TYPE: DNA
<213> ORGANISM: Artificial Sequence
<220> FEATURE:
<223> OTHER INFORMATION: primer, EF67SF

<400> SEQUENCE: 28
gtatcaccat caacacttct tccgttgaat acgacacccc g            41

<210> SEQ ID NO 29
<211> LENGTH: 20
<212> TYPE: DNA
<213> ORGANISM: Artificial Sequence
<220> FEATURE:
<223> OTHER INFORMATION: primer, EF67R

<400> SEQUENCE: 29
agaagtgttg atggtgatac                                    20

<210> SEQ ID NO 30
<211> LENGTH: 45
<212> TYPE: DNA
<213> ORGANISM: Artificial Sequence
<220> FEATURE:
<223> OTHER INFORMATION: primer, SP412X414XF
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t

<400> SEQUENCE: 30
gtgaagatca acatcttcnn saaannsgag ggcaagaacc tgctc         45

<210> SEQ ID NO 31
<211> LENGTH: 19
<212> TYPE: DNA
<213> ORGANISM: Artificial Sequence
<220> FEATURE:
<223> OTHER INFORMATION: primer, SP412414R

<400> SEQUENCE: 31
gaagatgttg atcttcacg                                     19

<210> SEQ ID NO 32
<211> LENGTH: 42
<212> TYPE: DNA
<213> ORGANISM: Artificial Sequence
<220> FEATURE:
<223> OTHER INFORMATION: primer, SP495X496XF
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 32
gagttcaagg tcaaggtgnn snnsgtcaga agtttaagcg ac            42

<210> SEQ ID NO 33

```
<211> LENGTH: 18
<212> TYPE: DNA
<213> ORGANISM: Artificial Sequence
<220> FEATURE:
<223> OTHER INFORMATION: primer, SP495496R

<400> SEQUENCE: 33
caccttgacc ttgaactc                                                        18

<210> SEQ ID NO 34
<211> LENGTH: 42
<212> TYPE: DNA
<213> ORGANISM: Artificial Sequence
<220> FEATURE:
<223> OTHER INFORMATION: primer, SP263F

<400> SEQUENCE: 34
caatttggct ttacaaactt tgaattcatt cctgatgaaa ag                              42

<210> SEQ ID NO 35
<211> LENGTH: 20
<212> TYPE: DNA
<213> ORGANISM: Artificial Sequence
<220> FEATURE:
<223> OTHER INFORMATION: primer, EF67R

<400> SEQUENCE: 35
agaagtgttg atggtgatac                                                      20

<210> SEQ ID NO 36
<211> LENGTH: 41
<212> TYPE: DNA
<213> ORGANISM: Artificial Sequence
<220> FEATURE:
<223> OTHER INFORMATION: primer, EF67AN

<400> SEQUENCE: 36
gtatcaccat caacacttct gcggttgaat acgacacccc g                              41

<210> SEQ ID NO 37
<211> LENGTH: 20
<212> TYPE: DNA
<213> ORGANISM: Artificial Sequence
<220> FEATURE:
<223> OTHER INFORMATION: primer, EF67C

<400> SEQUENCE: 37
agaagtgttg atggtgatac                                                      20

<210> SEQ ID NO 38
<211> LENGTH: 39
<212> TYPE: DNA
<213> ORGANISM: Artificial Sequence
<220> FEATURE:
<223> OTHER INFORMATION: primer, EF216AN

<400> SEQUENCE: 38
ccgttcctgc tgccgatcgc gggggtatac tccatctcc                                 39

<210> SEQ ID NO 39
<211> LENGTH: 18
<212> TYPE: DNA
<213> ORGANISM: Artificial Sequence
<220> FEATURE:
<223> OTHER INFORMATION: primer, EF216C

<400> SEQUENCE: 39
```

-continued

```
gatcggcagc aggaacgg                                              18

<210> SEQ ID NO 40
<211> LENGTH: 39
<212> TYPE: DNA
<213> ORGANISM: Artificial Sequence
<220> FEATURE:
<223> OTHER INFORMATION: primer, EF219AN

<400> SEQUENCE: 40
ctgccgatca acggggtagc gtccatctcc ggtcgtggt                       39

<210> SEQ ID NO 41
<211> LENGTH: 18
<212> TYPE: DNA
<213> ORGANISM: Artificial Sequence
<220> FEATURE:
<223> OTHER INFORMATION: primer, EF219C

<400> SEQUENCE: 41
taccccgttg atcggcag                                              18

<210> SEQ ID NO 42
<211> LENGTH: 38
<212> TYPE: DNA
<213> ORGANISM: Artificial Sequence
<220> FEATURE:
<223> OTHER INFORMATION: primer, EF229AN

<400> SEQUENCE: 42
ggtcgtggta ccgttgttgc gggtcgtgta gaacgcgg                        38

<210> SEQ ID NO 43
<211> LENGTH: 18
<212> TYPE: DNA
<213> ORGANISM: Artificial Sequence
<220> FEATURE:
<223> OTHER INFORMATION: primer, EF229C

<400> SEQUENCE: 43
aacaacggta ccacgacc                                              18

<210> SEQ ID NO 44
<211> LENGTH: 38
<212> TYPE: DNA
<213> ORGANISM: Artificial Sequence
<220> FEATURE:
<223> OTHER INFORMATION: primer, EF274AN

<400> SEQUENCE: 44
gaaggccgtg ctggtgaggc ggtaggtgtt ctgctgcg                        38

<210> SEQ ID NO 45
<211> LENGTH: 18
<212> TYPE: DNA
<213> ORGANISM: Artificial Sequence
<220> FEATURE:
<223> OTHER INFORMATION: primer, EF274C

<400> SEQUENCE: 45
ctcaccagca cggccttc                                              18

<210> SEQ ID NO 46
<211> LENGTH: 39
<212> TYPE: DNA
```

```
<213> ORGANISM: Artificial Sequence
<220> FEATURE:
<223> OTHER INFORMATION: primer, E216XN
<220> FEATURE:
<221> NAME/KEY: misc_feature
<222> LOCATION: (19)..(20)
<223> OTHER INFORMATION: n is a, c, g, or t

<400> SEQUENCE: 46
ccgttcctgc tgccgatcnn sggggtatac tccatctcc                              39

<210> SEQ ID NO 47
<211> LENGTH: 18
<212> TYPE: DNA
<213> ORGANISM: Artificial Sequence
<220> FEATURE:
<223> OTHER INFORMATION: primer, E216C

<400> SEQUENCE: 47
gatcggcagc aggaacgg                                                     18

<210> SEQ ID NO 48
<211> LENGTH: 19
<212> TYPE: DNA
<213> ORGANISM: Artificial Sequence
<220> FEATURE:
<223> OTHER INFORMATION: primer, DuetF

<400> SEQUENCE: 48
gggatctcga cgctctccc                                                    19

<210> SEQ ID NO 49
<211> LENGTH: 39
<212> TYPE: DNA
<213> ORGANISM: Artificial Sequence
<220> FEATURE:
<223> OTHER INFORMATION: primer, DuetSepTR

<400> SEQUENCE: 49
cccctagact accccggcct taactaatat actaagatg                              39

<210> SEQ ID NO 50
<211> LENGTH: 18
<212> TYPE: DNA
<213> ORGANISM: Artificial Sequence
<220> FEATURE:
<223> OTHER INFORMATION: primer, SepTF

<400> SEQUENCE: 50
gccggggtag tctagggg                                                     18

<210> SEQ ID NO 51
<211> LENGTH: 34
<212> TYPE: DNA
<213> ORGANISM: Artificial Sequence
<220> FEATURE:
<223> OTHER INFORMATION: primer, SepTBglR

<400> SEQUENCE: 51
tgcctgaact agatcttgga gccggggtg ggat                                    34

<210> SEQ ID NO 52
<211> LENGTH: 155
<212> TYPE: PRT
<213> ORGANISM: Artificial Sequence
<220> FEATURE:
<223> OTHER INFORMATION: H3S10ph protein having a His tag and a TEV
``` protease recognition sequence at the N-terminus

<400> SEQUENCE: 52

```
Met Gly Ser Ser His His His His His His Ser Gln Asp Pro Glu Asn
1               5                   10                  15

Leu Tyr Phe Gln Gly Arg Thr Lys Gln Thr Ala Arg Lys Ser Thr Gly
            20                  25                  30

Gly Lys Ala Pro Arg Lys Gln Leu Ala Thr Lys Ala Ala Arg Lys Ser
        35                  40                  45

Ala Pro Ala Thr Gly Gly Val Lys Lys Pro His Arg Tyr Arg Pro Gly
    50                  55                  60

Thr Val Ala Leu Arg Glu Ile Arg Arg Tyr Gln Lys Ser Thr Glu Leu
65                  70                  75                  80

Leu Ile Arg Lys Leu Pro Phe Gln Arg Leu Val Arg Glu Ile Ala Gln
            85                  90                  95

Asp Phe Lys Thr Asp Leu Arg Phe Gln Ser Ser Ala Val Met Ala Leu
            100                 105                 110

Gln Glu Ala Ser Glu Ala Tyr Leu Val Ala Leu Phe Glu Asp Thr Asn
        115                 120                 125

Leu Cys Ala Ile His Ala Lys Arg Val Thr Ile Met Pro Lys Asp Ile
    130                 135                 140

Gln Leu Ala Arg Arg Ile Arg Gly Glu Arg Ala
145                 150                 155
```